United States Patent
Ulmansky et al.

(10) Patent No.: US 9,883,369 B2
(45) Date of Patent: Jan. 30, 2018

(54) SYSTEM AND METHOD FOR PROVIDING ASSISTANCE DURING MEDICAL EMERGENCY

(71) Applicant: SONY CORPORATION, Tokyo (JP)

(72) Inventors: Asaf Ulmansky, Tel Aviv (IL); Adi Goren, Tel Aviv (IL)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/881,386

(22) Filed: Oct. 13, 2015

(65) Prior Publication Data
US 2017/0105104 A1 Apr. 13, 2017

(51) Int. Cl.
| | | |
|---|---|---|
| H04M 11/04 | (2006.01) |
| H04W 4/22 | (2009.01) |
| H04L 29/08 | (2006.01) |
| H04W 4/00 | (2009.01) |
| H04B 1/3822 | (2015.01) |
| H04W 4/04 | (2009.01) |
| A61B 5/00 | (2006.01) |

(52) U.S. Cl.
CPC ............. *H04W 4/22* (2013.01); *A61B 5/0022* (2013.01); *H04B 1/3822* (2013.01); *H04L 67/303* (2013.01); *H04L 67/306* (2013.01); *H04W 4/005* (2013.01); *H04W 4/046* (2013.01)

(58) Field of Classification Search
CPC ....... H04W 4/22; H04W 4/046; H04W 4/005; H04L 67/306; H04B 1/3822
USPC ........................................ 455/404.2; 370/338
See application file for complete search history.

(56) References Cited

U.S. PATENT DOCUMENTS

| | | | |
|---|---|---|---|
| 7,692,552 B2 | 4/2010 | Harrington et al. |
| 2012/0112879 A1 | 5/2012 | Ekchian et al. |
| 2013/0070043 A1 | 3/2013 | Geva et al. |
| 2014/0222446 A1* | 8/2014 | Ash ......... G06Q 50/22 |
| | | | 705/2 |
| 2014/0240132 A1 | 8/2014 | Bychkov |
| 2014/0275834 A1 | 9/2014 | Bennett |
| 2015/0302539 A1* | 10/2015 | Mazar ........ G08B 21/0211 |
| | | | 705/3 |
| 2016/0071418 A1* | 3/2016 | Oshida .......... G08G 1/22 |
| | | | 701/23 |
| 2016/0285974 A1* | 9/2016 | Shurtleff ......... H04L 67/12 |

OTHER PUBLICATIONS

Fujitsu, "Wearable Sensor Supports Drivers by Detecting Drowsiness in Advance", Fujitsu Journal, http://journal.jp.fujitsu.com/en/2015/02/03/01/, Feb. 3, 2015, pp. 4.

(Continued)

*Primary Examiner* — Marcos Batista
(74) *Attorney, Agent, or Firm* — Chip Law Group

(57) ABSTRACT

Various aspects of a system and method to provide assistance during a medical emergency are disclosed herein. The system comprises one or more circuits in an electronic device configured to receive sensor data associated with a user from one or more sensing devices. A change in health condition of the user is detected based on the received sensor data. Alert information that corresponds to the detected change is communicated to one or more other electronic devices associated with one or more other users. The one or more other users are selected based on profiles of the one or more other users.

4 Claims, 8 Drawing Sheets

(56) References Cited

OTHER PUBLICATIONS

Barton Morris, "The SCRAM Tether, How It Works and How It Doesn't", http://michigancriminalattorney.com/scram-tether-works/, Nov. 26, 2012, pp. 8.
Colin Bird, Ford Wants to Help Monitor Your Health, http://www.newsday.com/classifieds/cars/ford-wants-to-help-monitor-your-health-1.2899754, May 20, 2011, p. 1.
Pollen.com, Pollen.com's Allergy Alert iPhone & iPod App, http://www.pollen.com/ford-sync.asp, Retrieved on May 29, 2015, pp. 3.

* cited by examiner

SYSTEM AND METHOD FOR PROVIDING ASSISTANCE DURING MEDICAL EMERGENCY

FIELD

Various embodiments of the disclosure relate to a system and method to provide assistance during a medical emergency. More specifically, various embodiments of the disclosure relate to a system and method to provide assistance during a medical emergency based on data received from sensing devices.

BACKGROUND

Currently, the role of sensing devices has expanded beyond traditional fields, such as temperature measurement. Attempts have been made to develop, miniaturize, and/or customize various sensing devices for use in healthcare. Various sensing devices, such as a bio-compatible electronic sensor implanted into a body of a user and other wearable devices, may provide heath related sensor data. Further, some sensing devices may also be customized for use in vehicular environment to detect health condition of the user when the user is within the vehicle.

In certain instances, the user may experience a medical emergency while driving the vehicle. In such instances, it may be desired that a quick, reliable, and adequate assistance is provided to the impaired user. A smart system may be required to process such sensor data and other information associated with the user to ensure safety of the user, such as a driver of the vehicle, and to intelligently manage the medical emergency situation.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

A system and method to provide assistance during a medical emergency substantially as shown in, and/or described in connection with, at least one of the figures, as set forth more completely in the claims.

These and other features and advantages of the present disclosure may be appreciated from a review of the following detailed description of the present disclosure, along with the accompanying figures in which like reference numerals refer to like parts throughout.

DETAILED DESCRIPTION

The following described implementations may be found in the disclosed system and method to provide assistance during a medical emergency. Exemplary aspects of the disclosure may comprise a method that may receive sensor data associated with a user from one or more sensing devices. A change in health condition of the user may be detected based on the received sensor data. Alert information that corresponds to the detected change may be communicated to one or more other electronic devices associated with one or more other users. The one or more other users may be selected based on profiles of the one or more other users.

Figure 1:
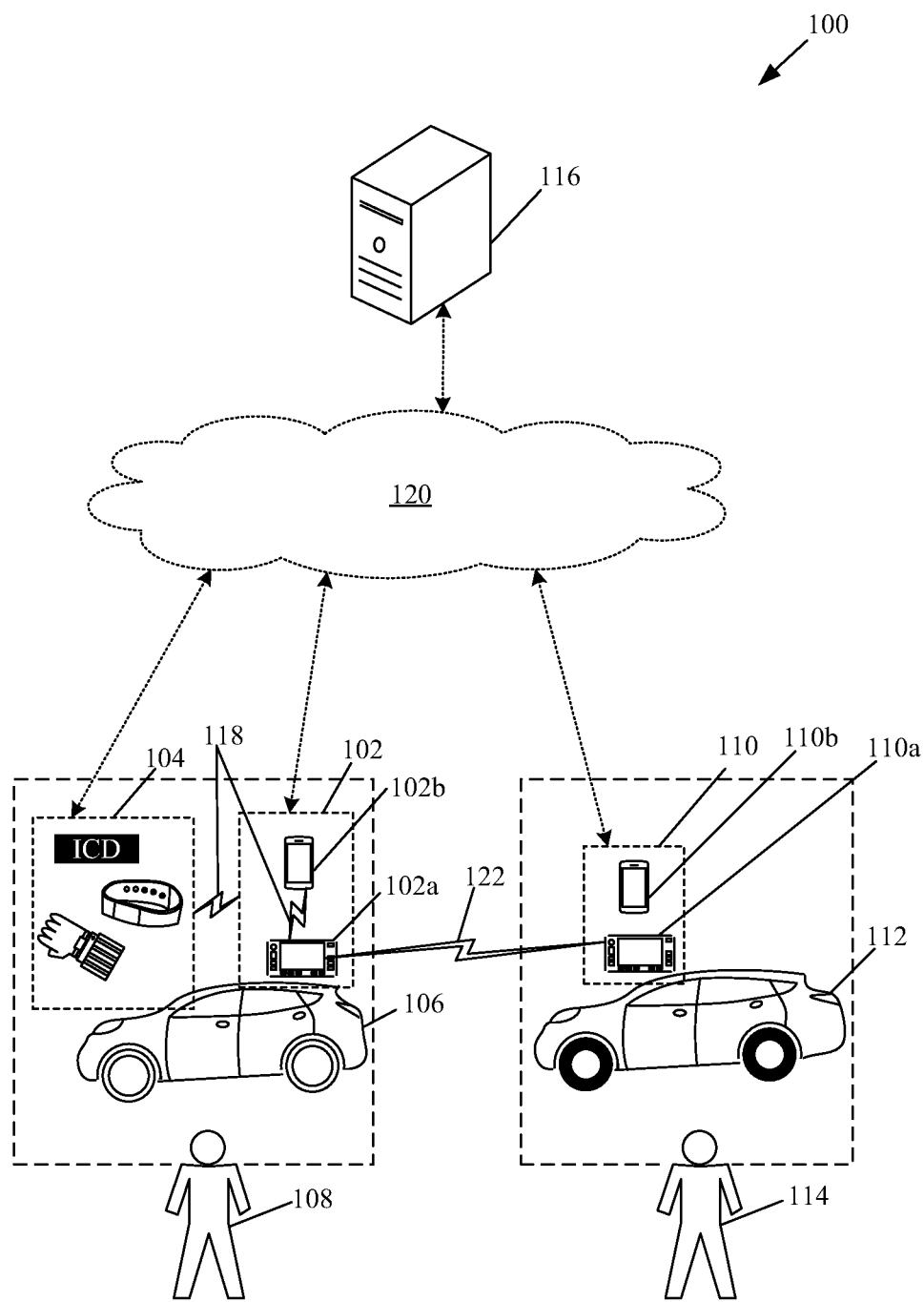
FIG. 1 is a block diagram that illustrates a network environment, in accordance with an embodiment of the disclosure.

FIG. 1 is a block diagram that illustrates a network environment, in accordance with an embodiment of the disclosure. With reference to FIG. 1, there is shown a network environment 100. The network environment 100 may include an electronic device 102, one or more sensing devices 104, and a vehicle 106, associated with a user, such as a driver 108. As examples of the electronic device 102, there is shown an in-vehicle infotainment (IVI) device 102*a* and a mobile device 102*b* associated with the driver 108. The network environment 100 may further include another electronic device 110 and another vehicle 112, associated with another user, such as a caregiver 114. As examples of the other electronic device 110, there is shown another in-vehicle infotainment device 110*a* and another mobile device 110*b*, associated with the caregiver 114. In accordance with an embodiment, the network environment 100 may also include one or more servers, such as a server 116, and one or more communication networks, such as a first communication network 118, a second communication network 120, and a vehicular communication network 122.

The electronic device 102 may be communicatively coupled to the one or more sensing devices 104, via the first communication network 118. The electronic device 102 may be communicatively coupled to one or more servers, such as the server 116, via the second communication network 120. The electronic device 102 may be configured to communicate with one or more other electronic devices, such as the other electronic device 110 in the other vehicle 112, via for example, the vehicular communication network 122 (such as a vehicle-to-vehicle (V2V) communication), the second communication network 120.

The electronic device 102 may comprise suitable logic, circuitry, interfaces, and/or code that may be configured to receive sensor data associated with the driver 108 from the one or more sensing devices 104. Examples of the electronic device 102 may include, but are not limited to, the IVI device 102*a*, an electronic control unit (ECU) used in the vehicle 106, a server, the mobile device 102*b*, such as a smartphone, and/or a wearable device, such as a smart watch. The IVI device 102*a* may correspond to an IVI system that provides entertainment and information content in a vehicle, such as the vehicle 106. The IVI device 102a will be described in detail in FIG. 2.

The one or more sensing devices 104 may comprise suitable logic, circuitry, interfaces, and/or code that may be configured to communicate sensor data to the electronic device 102, such as the IVI device 102a. The one or more sensing devices 104 may be one or more wearable devices worn by the driver 108, an electronic sensor implanted in the driver 108, and/or one or more in-vehicle sensors installed in the vehicle 106. Examples of the one or more wearable devices and the implanted electronic sensor (hereinafter referred to as implantable device) include, but are not limited to, a smart-glass, a smart-band, and/or a smart-watch, a nicotine patch, a motion sickness patch, an iontophoresis patch that uses electrical current for transdermal delivery of a drug, a glucose monitor, a wearable cardiac-event recorder, a bio-compatible sensor attached, worn, or implanted into to a human body to predict ovulation cycle, monitor health parameters, such as heart rate, pulse oximetry, respiratory rate, and/or blood pressure, a class II implantable device per the Food and Drug Administration (FDA) of United States of America (U.S.), implantable radio frequency device, such as a microchip implant, for patient identification and health information, and/or other wearable or implantable device that may provide diagnostic and therapeutic options for various illnesses and medical conditions. The one or more wearable devices and the implantable devices may be used by the driver 108 for healthcare purpose or for wellness and fitness tracking purpose. Examples of the one or more in-vehicle sensors may include, but are not limited to, sensors installed on a steering wheel, a seat belt, and/or a vehicle seat to detect a health condition of the driver 108 on-the-go.

The vehicle 106 may comprise one or more electronic control units (ECUs) and the IVI device 102a, which may communicate with the electronic device 102. The vehicle 106 may operate in an autonomous mode, a semi-autonomous mode, or a manual mode. Examples of vehicle 106 may include, but are not limited to, a motor vehicle, a hybrid vehicle, and/or a vehicle that uses one or more distinct renewable or non-renewable power sources. A vehicle that uses renewable or non-renewable power sources may include a fossil fuel-based vehicle, an electric propulsion-based vehicle, a hydrogen fuel-based vehicle, a solar-powered vehicle, and/or a vehicle powered by other forms of alternative energy sources.

The other electronic device 110 may comprise suitable logic, circuitry, interfaces, and/or code that may be configured to receive alert information from the electronic device 102. The alert information may correspond to a change in health condition of the driver 108 of the vehicle 106. Examples of the other electronic device 110 may include, but are not limited to, the other IVI device 110a, the other mobile device 110b, an electronic control unit (ECU) used in the other vehicle 112, and/or a wearable device, associated with the caregiver 114. In accordance with an embodiment, the other electronic device 110 may include the other mobile device 110b (or a portable device) to connect to the other IVI device 110a to transfer a user profile, such as a profile of the caregiver 114, from the other mobile device 110b to the other IVI device 110a of the other vehicle 112.

The other vehicle 112 may be similar to that of the vehicle 106, and may operate in an autonomous mode, a semi-autonomous mode, or a manual mode. The other vehicle 112 may comprise one or more electronic control units (ECUs) and the other IVI device 110a, which may communicate with the IVI device 102a and/or an ECU of the vehicle 106, via the vehicular communication network 122, such as a vehicle-to-vehicle (V2V) communication.

The caregiver 114 may be a person or an entity, such as a registered physician and/or a registered medical assistant, associated with one of the emergency medical services. The caregiver 114 may provide out-of-hospital emergency medical services, such as a roadside medical assistance, to the driver 108, during a medical emergency.

The server 116 may comprise suitable logic, circuitry, interfaces, and/or code that may be configured to receive alert information from the electronic device 102 associated with the driver 108. The alert information may correspond to a detected change in a health condition of a user, such as the driver 108, of the vehicle 106. The server 116 may be configured to establish communication with one or more other electronic devices, such as the other electronic device 110, associated with one or more caregivers (such as the caregiver 114). The server 116 may be a web server, a database server, a file server, an application server, or a combination thereof. The server 116 may be implemented by use of several technologies that are well known to those skilled in the art.

The first communication network 118 may include a medium through which the one or more sensing devices 104 may communicate with the electronic device 102. Examples of the first communication network 118 may include, but are not limited to, a short range network, such as a 2-way radio frequency network (such as a Bluetooth-based network), a Wireless Personal Area Network (WPAN), and/or a Wireless Local Area Network (WLAN). The one or more sensing devices 104 may be operable to connect to the electronic device 102, in the first communication network 118, in accordance with various wired or wireless communication protocols or interoperability standards related to health informatics. Examples of such wired or wireless communication protocols or technical standards may include, but are not limited to, International Organization for Standardization's (ISO) Technical Committee (TC) on health informatics (ISO/TC 215), ISO/IEEE-11073 personal health data (PHD) standards, technical standards of continua (associated with Continua Health Alliance), Health Level-7 (HL7) standards, ISO 27799, ISO 17115, ISO/TR 16056-1 and 2, ISO/TS 16058, Bluetooth protocol, an infrared protocol, a Wireless Fidelity (Wi-Fi) protocol, a ZigBee protocol, IEEE 802.11, 802.16, cellular communication protocols, a Near Field Communication (NFC) protocol, a Universal Serial Bus (USB) protocol, and/or a wireless USB protocol. In accordance with an embodiment, the in-vehicle sensors of the one or more sensing devices 104 may communicate with the electronic device 102, such as the IVI device 102a, via an in-vehicle network, such as a controller area network (CAN) protocol and/or Ethernet (described in detail in FIG. 2).

The second communication network 120 may include a wireless medium through which the electronic device 102 may communicate with one or more servers, such as the server 116, and external communication mediums associated with one or more of emergency services providers. Examples of the second communication network 120 may include, but are not limited to, the Internet, a cloud network, a Local Area Network (LAN), a telephone line (POTS), a Metropolitan Area Network (MAN), a Wireless Local Area Network (WLAN), and/or a cellular network, such as a long-term evolution (LTE) 3G and/or 4G network. Various devices in the network environment 100 may be operable to connect to the second communication network 120, in accordance with various wireless communication protocols.

Examples of such wireless communication protocols, communication standards, and technologies may include, but are not limited to, IEEE 802.11, 802.15, 802.16, Transmission Control Protocol and Internet Protocol (TCP/IP), User Datagram Protocol (UDP), Hypertext Transfer Protocol (HTTP), Long-term Evolution (LTE), File Transfer Protocol (FTP), Enhanced Data GSM Environment (EDGE), voice over Internet Protocol (VoIP), a protocol for email, instant messaging, and/or Short Message Service (SMS), and/or cellular communication protocols.

The vehicular communication network 122 may include a wireless medium through which the electronic device 102 associated with the vehicle 106 may communicate with one or more other electronic devices, such as an ECU of the other vehicle 112. In accordance with an embodiment, the vehicular communication network 122 may correspond to a vehicle-to-vehicle (V2V) communication. Examples of the vehicular communication network 122 may include, but are not limited to, a dedicated short-range communication (DSRC) network, a vehicular ad-hoc network (VANET), Intelligent vehicular ad-hoc network (InVANET), Internet based mobile ad-hoc networks (IMANET), a mobile ad-hoc network (MANET), a wireless sensor network (WSN), a wireless mesh network (WMN), a Wireless Local Area Network (WLAN), and/or a cellular network, such as a long-term evolution (LTE) 3G and/or 4G network. Various examples of such wireless communication protocols, communication standards, and technologies may include, but are not limited to, 802.11p, 1609, Worldwide Interoperability for Microwave Access (Wi-MAX), DSRCprotocol, Wireless Access in Vehicular Environments (WAVE), Long-term Evolution (LTE), and/or other cellular communication protocols.

In operation, the electronic device 102 may be configured to receive sensor data associated with a user, such as the driver 108, from the one or more sensing devices 104. In accordance with an embodiment, the electronic device 102 may be configured to detect a change in the health condition of the driver 108, based on the received sensor data. The detected change may be an abnormal change that may be detected when the received sensor data (that corresponds to the health parameters of the driver 108) is not within normal limits or not in accordance with one or more pre-defined medical safety limits. For example, an acute myocardial infarction (a heart attack) may be detected when the received sensor data indicates very high cardiac rhythms, and/or high blood pressure. In another example, an occurrence of hyperhidrosis localized to a certain body area, such as palm of the driver 108 as detected by a sensor located at a steering wheel of the vehicle 106, may also indicate the detected abnormal condition. In yet another example, an in-vehicle sensor of the one or more sensing devices 104 may be located on a seat belt of the vehicle 106 to monitor heart rate.

In accordance with an embodiment, the detection of the change in the health condition of the driver 108 may be further based on a health profile of the driver 108. The health profile may include medical history data of the driver 108. The medical history data may correspond to self-declaration of medical information by the driver 108. In accordance with an embodiment, the medical history data may also include personal heath data of the driver 108 that may be digitally stored in an implant, such as a microchip implant, in a secured manner.

In accordance with an embodiment, the electronic device 102 may be configured to select one or more caregivers, such as the caregiver 114, based on profiles of the one or more caregivers. The selected one or more caregivers may correspond to the one or more other users associated with the one or more other electronic devices, such as the other electronic device 110. The selected one or more caregivers, such as the caregiver 114, may indicate one or more potential and/or relevant caregivers that may provide assistance in a medical emergency associated with the detected change in the health condition of the driver 108. In accordance with an embodiment, the selection of the one or more caregivers, such as the caregiver 114, may be based on detected change in the health condition of the driver 108 and relative distance information of the one or more caregivers from the driver 108.

The profiles of the one or more caregivers may correspond to pre-stored profiles of a group of caregivers. The profiles of the group of caregivers that also include the profiles of the one or more caregivers, such as the profile of the caregiver 114, may comprise information related to an expertise level, a type of expertise, current position, and/or availability associated with each caregiver of the group of caregivers. In accordance with an embodiment, the profiles of the group of caregivers (such as pre-stored profiles of all caregivers) may be stored at the electronic device 102.

In accordance with an embodiment, the electronic device 102 may be configured to communicate alert information to one or more other electronic devices, such as the other electronic device 110, associated with the selected one or more caregivers, such as the caregiver 114. The alert information may be communicated to the one or more other electronic devices, such as the other electronic device 110, via the second communication network 120 and/or the vehicular communication network 122.

In accordance with an embodiment, the electronic device 102 may be configured to communicate the alert information to one or more vehicles associated with the one or more caregivers, via the vehicular communication network 122, such as V2V communication. The communicated alert information may include metadata associated with the detected change in the health condition of the driver 108 and current location of the driver 108. In accordance with an embodiment, the metadata may comprise one or more health parameters of the driver 108 received prior to, during, and/or post the detected change in the health condition of the driver 108. The communicated alert information may also include a video of the driver 108 captured by in-vehicle sensors, such as an image sensor, of the one or more sensing devices 104. The video may indicate the health condition of the driver 108 in a medical emergency situation associated with the driver 108, such as sudden experience of a heart attack.

In accordance with an embodiment, the electronic device 102 may be configured to communicate the alert information (that corresponds to the detected change in the health condition of the driver 108) to the server 116, via the second communication network 120. In such a case, the server 116 may be configured to receive the alert information from the electronic device 102 associated with the driver 108. The server 116 may be configured to determine one or more other electronic devices, such as the other electronic device 110, associated with one or more caregivers, such as the caregiver 114, to communicate the received alert information. Such determination may be based on the profiles of one or more caregivers that correspond to a group of caregivers. The server 116 may be configured to communicate the received alert information to the determined one or more other electronic devices associated with the one or more caregivers, such as the caregiver 114. The communicated alert information may enable the selected one or more caregivers, such as the caregiver 114, to be ready to provide a first aid to the driver 108. The caregiver 114 may be a registered physician who may traverse in the other vehicle 112, nearby to the vehicle 106 driven by the impaired driver 108. Accordingly, the caregiver 114 may be ready to provide a quick assistance to the driver 108 when the driver 108 stops the vehicle 106. Thus, the time to understand the heath condition of the driver 108 and/or provision of the first aid on arrival of the caregiver 114 may be shortened due to the communicated alert information.

In accordance with an embodiment, the one or more other electronic devices, such as the other electronic device 110, may be configured to receive the alert information from the electronic device 102, such as the IVI device 102a, or from the server 116. The alert information may be received via the vehicular communication network 122 (such as the V2V communication, the second communication network 120, and/or other such communication network). The received alert information may correspond to the detected change in health condition of the driver 108. The other electronic device 110, such as the other IVI device 110a, may be configured to customize the received alert information based on a profile of the caregiver 114.

In accordance with an embodiment, instead of the other IVI device 110a, the alert information may be received by the other mobile device 110b, such as a smartphone, associated with the caregiver 114. In such an embodiment, the other mobile device 110b may be configured to customize the received alert information based on the profile of the caregiver 114. The received alert information may be customized to generate instruction information for the driver 108. The generated instruction information may be subsequently transferred to the other IVI device 110a for further communication to the driver 108. The generated instruction information may be communicated to the electronic device 102 associated with the driver 108. Alternatively, the generated instruction information may be communicated to the server 116.

In accordance with an embodiment, the server 116 may be configured to receive instruction information from the one or more other electronic devices, such as the other electronic device 110, in response to the communicated alert information. In accordance with an embodiment, the instruction information may be based on the health profile of the driver 108. The health profile may include pre-defined information regarding a pre-existing health disorder, such as diabetes. The server 116 may be configured to communicate the received instruction information to the electronic device 102 associated with the driver 108.

In accordance with an embodiment, the electronic device 102 may be configured to receive instruction information from the server 116, and/or the one or more other electronic devices, such as the other electronic device 110 associated with the caregiver 114. The instruction information may be received in response to the communicated alert information.

In accordance with an embodiment, the electronic device 102 may be configured to communicate the received instruction information to the driver 108, in response to the detected change in the health condition of the driver 108. The instruction information may be audio, text and/or video instructions. The output may be generated via a wearable device of the one or more sensing devices 104, the mobile device 102b, and/or a speaker communicatively coupled to the IVI device 102a. For example, the mobile device 102b may output the instruction information as an audio message, to instruct the driver 108 to stop the vehicle 106 at a safe location along a road portion.

Figure 2:
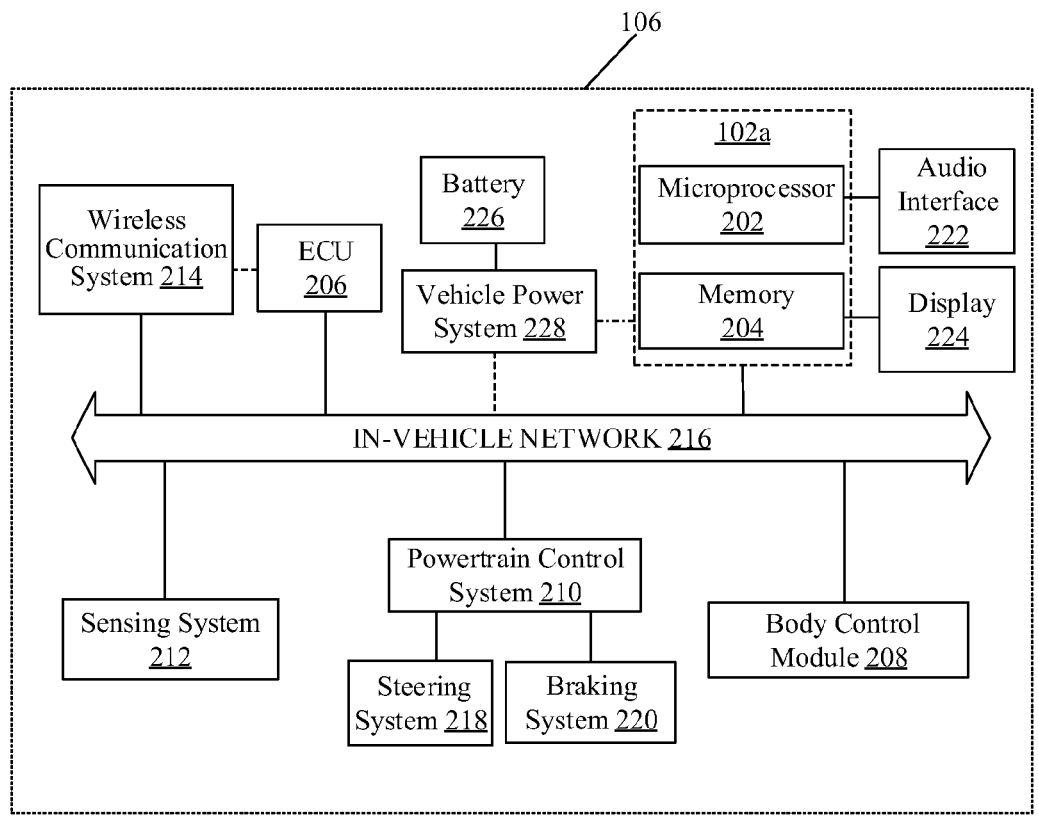
FIG. 2 is a block diagram that illustrates an exemplary electronic device and various exemplary components or systems of a vehicle, in accordance with an embodiment of the disclosure.

FIG. 2 is a block diagram that illustrates an exemplary electronic device and various exemplary components or systems of a vehicle, in accordance with an embodiment of the disclosure. FIG. 2 is explained in conjunction with elements from FIG. 1. With reference to FIG. 2, there is shown the IVI device 102a as an example of the electronic device 102, and various other control units, systems or components of the vehicle 106. The vehicle 106 may comprise the IVI device 102a that may include the microprocessor 202 and the memory 204. The vehicle 106 may further comprise an electronic control unit (ECU) 206, a body control module 208, a powertrain control system 210, a sensing system 212, a wireless communication system 214, and an in-vehicle network 216. There is further shown a steering system 218 and a braking system 220 associated with the powertrain control system 210. There is further shown an audio interface 222 and a display 224 associated with the IVI device 102a, and a battery 226 associated with a vehicle power system 228. In accordance with an embodiment, the audio interface 222, the display 224, and the wireless communication system 214 may also be associated with the ECU 206.

The IVI device 102a, the various control units, components, or systems may be communicatively coupled to each other, via the in-vehicle network 216, such as an in-vehicle data bus. The in-vehicle network 216 may correspond to one or more in-vehicle networks, such as a controller area network (CAN), a Local Interconnect Network (LIN), Ethernet, and/or a Media Oriented Systems Transport (MOST) based network (described in details below). It should be understood that the vehicle 106 may also include other suitable components or systems, but for brevity, those components, or systems, which are used to describe and explain the function and operation of the present disclosure, are illustrated herein.

The IVI device 102a may comprise suitable logic, circuitry, interfaces, and/or code that may be configured to receive sensor data, via the first communication network 118, from the one or more sensing devices 104 associated with the driver 108. The IVI device 102a may be communicatively coupled to other ECUs, such as the ECU 206, and/or control systems of the vehicle 106. The IVI device 102a may comprise the microprocessor 202 and the memory 204.

The microprocessor 202 may comprise suitable logic, circuitry, interfaces, and/or code that may be configured to execute a set of instructions stored in the memory 204. The microprocessor 202 may be configured to register the one or more wearable devices or the implantable devices of the one or more sensing devices 104 associated with the driver 108. The registration may establish a communicative coupling of the electronic device 102 with the one or more wearable devices or the implantable devices associated with a user, such as the driver 108. Examples of the microprocessor 202 may be an X86-based processor, a Reduced Instruction Set Computing (RISC) processor, an Application-Specific Integrated Circuit (ASIC) processor, a Complex Instruction Set Computing (CISC) processor, an Explicitly Parallel Instruction Computing (EPIC) processor, a Very Long Instruction Word (VLIW) processor, a microcontroller, a central processing unit (CPU), a graphics processing unit (GPU), a state machine, and/or other processors or circuits.

The memory 204 may comprise suitable logic, circuitry, and/or interfaces that may be configured to store a machine code and/or a set of instructions with at least one code section executable by the microprocessor 202. The memory 204 may be configured to store an IVI application. Examples of implementation of the memory 204 may include, but are not limited to, Electrically Erasable Programmable Read-Only Memory (EEPROM), Random Access Memory (RAM), Read Only Memory (ROM), Hard Disk Drive (HDD), Flash memory, a Secure Digital (SD) card, Solid-State Drive (SSD), and/or CPU cache memory.

The ECU 206 may comprise suitable logic, circuitry, and/or interfaces that may be configured to receive sensor data associated with the driver 108 from the one or more sensing devices 104, in accordance with an embodiment. The ECU 206 may be communicatively coupled to the IVI device 102a, via the in-vehicle network 216.

The body control module 208 may refer to another electronic control unit that comprises suitable logic, circuitry, interfaces, and/or code that may be configured to control a central door locking system of the vehicle 106. The body control module 208 may be configured to receive a command from the ECU 206. Subsequently, the body control module 208 may relay the command to other suitable vehicle systems or components, such as the central door locking system, for access control of the vehicle 106.

The powertrain control system 210 may refer to an onboard computer of the vehicle 106 that controls operations of an engine and a transmission system of the vehicle 106. The powertrain control system 210 may control the engine's ignition, fuel injection, emission systems, and/or operations of a transmission system (such as automatic transmission system) and the braking system 220.

The sensing system 212 may comprise one or more other vehicle sensors embedded in the vehicle 106. The sensing system 212 may be operatively connected to the IVI device 102a or the ECU 206, via the in-vehicle network 216. One or more network interfaces, such as a CAN interface, may be provided in the sensing system 212, to connect to the in-vehicle network 216. Examples of the one or more vehicle sensors of the sensing system 212 may include, but are not limited to, a radio detection and ranging (RADAR) device, a light detection and ranging (LIDAR) device, an image sensor or a camera, a vehicle speed sensor, an odometric sensor, a yaw rate sensor, a speedometer, a global positioning system (GPS), a steering angle detection sensor, a vehicle travel direction detection sensor, a magnometer, a touch sensor, an infrared sensor, and/or the in-vehicle sensors of the one or more sensing devices 104 to detect heath parameters of the user, such as the driver 108. The one or more vehicle sensors of the sensing system 212 may be configured to detect motion status, direction of travel, location information, steering angle, yaw rate, speed, and/or rate-of-change of speed of the vehicle 106.

The in-vehicle network 216 may include a medium through which the various control units, components, or systems of the vehicle 106, such as the IVI device 102a, the body control module 208, the powertrain control system 210, the sensing system 212, and/or the wireless communication system 214, may communicate with each other. In accordance with an embodiment, in-vehicle communication of audio/video data for multimedia components may occur by use of Media Oriented Systems Transport (MOST) multimedia network protocol of the in-vehicle network 216. The MOST-based network may be a separate network from the controller area network (CAN). The MOST-based network may use a plastic optical fiber (POF). In accordance with an embodiment, the MOST-based network, the CAN, and other in-vehicle networks may co-exist in a vehicle, such as the vehicle 106. The in-vehicle network 216 may facilitate access control and/or communication between the IVI device 102a, other internal ECUs (such as the ECU 206), and the control systems of the vehicle 106. One or more communication interfaces, such as the CAN interface, a Local Interconnect Network (LIN) interface, and/or Ethernet interface, may be used by the various components or systems of the vehicle 106 to connect to the in-vehicle network 216. The various control units, components, or systems of the vehicle 106, may use various wired and wireless communication protocols, such as controller area network (CAN), Local Interconnect Network (LIN), Ethernet or other communication protocols to connect to the in-vehicle network 216. Examples of the wired and wireless communication protocols for the in-vehicle network 216 may include, but are not limited to, a vehicle area network (VAN), a CAN bus, Domestic Digital Bus (D2B), Time-Triggered Protocol (TTP), FlexRay, IEEE 1394, Carrier Sense Group of Access With Collision Detection (CSMA/CD) based data communication protocol, Inter-Integrated Circuit ($I^2C$), Inter Equipment Bus (IEBus), Society of Automotive Engineers (SAE) J1708, SAE J1939, International Organization for Standardization (ISO) 11992, ISO 11783, Media Oriented Systems Transport (MOST), MOST25, MOST50, MOST150, Plastic optical fiber (POF), Power-line communication (PLC), and/or Serial Peripheral Interface (SPI) bus.

The steering system 218 may be associated with the powertrain control system 210. The steering system 218 may include a steering wheel and/or an electric motor (provided for a power-assisted steering) that may be used by a vehicle user, such as the driver 108, to control movement of the vehicle 106. In accordance with an embodiment, the movement or steering of the vehicle 106 may be automatically controlled when the vehicle 106 is in autonomous mode. Examples of the steering system 218 may include, but are not limited to, an autonomous steering control, a power-assisted steering system, a vacuum/hydraulic-based steering system, an electro-hydraulic power-assisted system (EH-PAS), or a "steer-by-wire" system, known in the art.

The braking system 220 may be used to stop or slow down the vehicle 106 by application of frictional forces. The braking system 220 may be configured to receive a command from the powertrain control system 210, under the control of the microprocessor 202, when the vehicle 106 is in an autonomous mode or a semi-autonomous mode.

The audio interface 222 may be connected to a speaker, a chime, a buzzer, or other device that may be operable to generate a sound. The audio interface 222 may also be connected to a microphone or other device to receive a voice input from an occupant, such as the driver 108, of the vehicle 106. The audio interface 222 may be a part of the IVI system, such as the IVI device 102a, or a head unit of the vehicle 106.

The display 224 may refer to a display screen to display various types of information to the occupants of the vehicle 106. The display 224 may be communicatively coupled to the IVI device 102a. In accordance with an embodiment, the display 224 may be a touch screen display that may receive an input from the driver 108. Examples of the display 224 may include, but are not limited to, a display of the head unit or the IVI device 102a, a heads-up display (HUD), a heads-up display with an augmented reality system (AR-HUD), a driver information console (DIC), a projection-based display, a see-through display, a smart-glass display, and/or an electro-chromic display. In accordance with an embodiment, the vehicle 106 may include other input/output (I/O) devices that may be configured to communicate with the microprocessor 202. The I/O devices may be configured to receive input from the driver 108, and/or provide output to the driver 108 in the vehicle 106.

The battery 226 may be source of electric power for one or more electric circuits or loads (not shown). The battery 226 may be a rechargeable battery. The battery 226 may be a source of electrical power to start an engine of the vehicle 106 by selectively providing electric power to an ignition system (not shown) of the vehicle 106. The battery 226 may also be a source of electrical power for the display 224, the IVI device 102a, and other loads. For example, the loads may include, but are not limited to various lights, such as headlights and interior cabin lights, electrically powered adjustable components, such as vehicle seats, mirrors, windows or the like, and/or other IVI systems, such as radio, speakers, electronic navigation system, electrically controlled, powered and/or assisted steering, such as the steering system 218.

The vehicle power system 228 may regulate the charging and the power output of the battery to various electric circuits and loads of the vehicle 106, as described above. When the vehicle 106 is a hybrid vehicle or an autonomous vehicle, the vehicle power system may provide the required voltage for all of the components and enable the vehicle 106 to utilize the battery power for a sufficient amount of time. In accordance with an embodiment, the vehicle power system may correspond to power electronics, and may include a microcontroller that may be communicatively coupled to the in-vehicle network 216. In such an embodiment, the microcontroller may receive command from the powertrain control system 210 under the control of the IVI device 102a or the ECU 206.

In operation, the microprocessor 202 may be configured to receive sensor data associated with a user, such as the driver 108, from the one or more sensing devices 104. The one or more sensing devices 104 may be communicatively coupled to the microprocessor 202, via the first communication network 118, such as Bluetooth network. For example, the driver 108 may wear the one or more wearable devices, such as a smart-band. The driver 108 may enter the vehicle 106 and may hold the steering wheel of the vehicle 106. The steering wheel may be fitted with the sweat sensor to detect sweating from palms of the driver 108. The one or more in-vehicle sensors of the one or more sensing devices 104 may also be pre-installed in the vehicle 106 to detect one or more health parameters of the driver 108 on-the-go. When the driver 108 enters the vehicle 106, a communicative coupling may be established between the microprocessor 202 and the one or more sensing devices 104, such as the smart-band and/or the in-vehicle sensors, by use of the IVI application pre-installed at the memory 204 of the IVI device 102a. In accordance with an embodiment, the pre-installation of the IVI application may correspond to an installation provided in a vehicle, such as the vehicle 106, at the time of purchase or at a later point in time after purchase. In accordance with an embodiment, a software update may be performed for the pre-installed IVI application.

In accordance with an embodiment, the microprocessor 202 may be configured to perform a login operation to confirm an identity of the driver 108 associated with the one or more sensing devices 104. In accordance with an embodiment, the login operation may be auto-login operation based on pre-registration of the one or more sensing devices 104, such as previously paired devices. Alternatively, a login password, a touch input (such as a finger scan), and/or other gesture input may be provided by the driver 108, via the IVI application, by use of the display 224 for the login operation. In accordance with an embodiment, the identity of the driver 108 may be confirmed based on voice recognition, face recognition, and/or car key identification. The microprocessor 202 may be configured to validate the driver 108 based on the pre-stored health profile of the driver 108. One or more messages, such as "Hello Jack, your identity is confirmed", may be generated to indicate successful login. Other heath advisory messages based on medical history data of the driver 108 may also be outputted. For example, the driver 108 may be a diabetic as per the heath profile of the driver 108. Accordingly, an advisory message, such as "Hi Jack! A quick reminder: Do you have a sugar-containing drink available with you today?", may be outputted via the I/O device, such as the speaker or the display 224 associated with the IVI device 102a.

In accordance with an embodiment, and in instances when the login operations fails after repeated attempts (such as 3 to 5 times login attempt), the microprocessor 202 may be configured to establish communicative coupling via the second communication network 120. The microprocessor 202 may log information related to the login failure event, such as time, location and/or a photograph of the user that may attempt to perform the login operation.

The microprocessor 202 may be configured to monitor vital health parameters of the driver 108, based on the sensor data received periodically from the one or more sensing devices 104. The received sensor data may indicate a health condition of the driver 108. The sensor data associated with the driver 108 may correspond to the health parameters, such as electrocardiogram (ECG), heart rate, respiratory rate, blood oxygen level (such as peripheral capillary oxygen saturation (SpO2)), blood pressure, and/or body temperature of the of the driver 108.

In accordance with an embodiment, the microprocessor 202 may be configured to check whether the received sensor data that includes the vital health parameters are within normal limits or in accordance with one or more pre-defined medical safety limits. The microprocessor 202 may be configured to detect a change in the health condition of the driver 108, based on the received sensor data. The detected change may be an abnormal change that may be detected when the received sensor data (that corresponds to the vital health parameters) is not within normal limits or in accordance with one or more pre-defined medical safety limits. For example, abnormal conditions, such as hyperglycemia, hyperhidrosis, tachycardia, heart failure, neurological disorder, hemorrhage, and/or other biological, chemical, and/or physical dysfunctions, such as a sudden onset of paralysis, associated with a user, such as the driver 108, may be detected based on the received sensor data.

In accordance with an embodiment, the detection of the change in the health condition of the driver 108 may be further based on a health profile of the driver 108. The health profile may include medical history data of the driver 108. The medical history data may correspond to self-declaration of medical information by the driver 108. In accordance with an embodiment, the medical history data may also include personal heath data of the driver 108 that may be digitally stored in an implant, such as a microchip implant, in a secured manner.

In accordance with an embodiment, the microprocessor 202 may be configured to select one or more caregivers, such as the caregiver 114, based on profiles of the one or more caregivers. The selected one or more caregivers, such as the caregiver 114, may indicate one or more potential and/or relevant caregivers that may provide assistance in a medical emergency associated with the detected change in the health condition of the driver 108. In accordance with an embodiment, the selection of the one or more caregivers, such as the caregiver 114, may be based on detected change in the health condition of the driver 108, and relative distance information of the one or more caregivers from the driver 108.

In accordance with an embodiment, the profiles of the one or more caregivers may be selected from a group of profiles of caregivers. The profiles of the caregivers, which also include the profile of the caregiver 114, may comprise information related to an expertise level, a type of expertise, current position, and/or availability associated with each caregiver of the group of caregivers. In accordance with an embodiment, the profiles of the caregivers may be stored at the memory 204. In accordance with an embodiment, the profiles of the caregivers may be dynamically updated based on vehicle data received from one or more connected vehicles in the vicinity of the vehicle 106. For example, the IVI device 102a or an ECU of the vehicle 106 may receive vehicle data of the other vehicle 112, via the vehicular communication network 122. In accordance with an embodiment, the vehicle data may be received when the other vehicle 112 is in vicinity of the vehicle 106. The vehicle data received from the other vehicle 112 may include a unique vehicle identifier, a vehicle position, a vehicle size, a direction of travel, and/or a vehicle speed value of the other vehicle 112. The received vehicle data may further include a rate-of-change of speed, lane information, a steering angle, a vehicle positional accuracy data, a brake system status, a status of a vehicle stability system, a yaw rate, and/or other vehicle parameters of the other vehicle 112.

In accordance with an embodiment, the microprocessor 202 may be configured to generate alert information that corresponds to the detected change in the health condition of the driver 108. In accordance with an embodiment, the microprocessor 202 may be configured to output the generated alert information for the driver 108 to indicate the detected change in the health condition of the driver 108. The output may be audio, text, haptic, and/or video output. The alert may help the driver 108 to know about the health status of the driver 108 on-the-go. Hence, self-awareness of the health status of the driver 108 may be improved.

In accordance with an embodiment, the microprocessor 202 may be configured to communicate the generated alert information to one or more other electronic devices, such as the other electronic device 110, associated with the selected one or more caregivers (selected caregivers), such as the caregiver 114. The communicated alert information may include metadata associated with the detected change in the health condition of the driver 108 and a current location of the driver 108. In accordance with an embodiment, the metadata may comprise one or more health parameters of the driver 108 received prior to, during, and/or post the detected change in the health condition of the driver 108, as described in FIG. 1. The one or more health parameters of the driver 108 received prior to, during, and/or post the detected change in the health condition of the driver 108, may also be useful as an evidence to seek a potential claim from an insurance company. For example, in case of occurrence of an accident or a self-accident by the driver 108 because of the abnormal heath condition (during the medical emergency) and/or a mistake of the driver 108 while driving the vehicle 106 during the medical emergency, the insurance company and/or the driver 108 may know exactly what happened and may have real evidence for the potential claims.

In accordance with an embodiment, the communicated alert information may also include a video of the driver 108 captured by in-vehicle sensors, such as an image sensor, of the one or more sensing devices 104. The video may indicate the health condition of the driver 108 in a medical emergency situation, such as the detected heart attack. The communicated alert information may enable the selected one or more caregivers, such as the caregiver 114, to be ready to prepare first aid to the driver 108, in advance. The time to provide the first aid to the driver 108 without further delay (that may otherwise occur to understand the medical situation) may be shortened.

In accordance with an embodiment, the microprocessor 202 may be configured to communicate the alert information to one or more vehicles associated with the one or more caregivers, via the vehicular communication network 122, such as the V2V communication. In accordance with an embodiment, the microprocessor 202 may be configured to communicate the alert information to one or more vehicles associated with other users that may not be the caregivers, via the vehicular communication network 122, such as the V2V communication. Such communication may aid in minimization of accidents of the vehicles (that may traverse nearby the vehicle 106) due to the impairment of the driver 108 who may then face a difficulty to drive in such deteriorated heath condition.

In accordance with an embodiment, the microprocessor 202 may be configured to communicate the alert information that corresponds to the detected change in the health condition of the driver 108 to the server 116, via the second communication network 120. In accordance with an embodiment, the microprocessor 202 may be configured to receive instruction information from the server 116, and/or the one or more other electronic devices, such as the other electronic device 110 associated with the caregiver 114. The instruction information may be received in response to the communicated alert information.

In accordance with an embodiment, the microprocessor 202 may be configured to communicate the instruction information to the driver 108, in response to the detected change in the health condition of the driver 108. The instruction information may be communicated as audio, text and/or video instructions. For example, the speaker or the display 224 may output the instruction information as an audio-visual message, to instruct the driver 108 to stop the vehicle 106 at a safe location along a road portion. In accordance with an embodiment, the output may be generated via a wearable device of the one or more sensing devices 104 and/or the mobile device 102b, such as a smartphone. In accordance with an embodiment, the instruction information may be generated based on the health profile of the driver 108. The health profile may include pre-defined information regarding pre-existing health disorder, such as diabetes, of the driver 108.

In accordance with an embodiment, the alert information may be communicated at one or more time instances for a pre-defined duration, such as "every 10 seconds for 30 seconds". The communication at the one or more time instances may occur while the driver 108 is driving the vehicle 106. In accordance with an embodiment, the microprocessor 202 may be configured to further select one or more other caregivers, such as another caregiver different from the caregiver 114, based on updated location of the driver 108 at a subsequent time instance. The selection may be further based on profiles of the one or more other caregivers. The selected one or more other caregivers may be in a vicinity of the updated location of the driver 108 while the driver 108 drives the vehicle 106. The microprocessor 202 may then communicate the alert information to one or more other electronic devices associated with the selected one or more other caregivers. The communication of the alert information may occur for the pre-determined time interval.

In accordance with an embodiment, the microprocessor 202 may be configured to receive one or more responses from the one or more other electronic devices, such as the other electronic device 110, associated with the selected one or more other users (such as the one or more caregivers). In accordance with an embodiment, the microprocessor 202 may be configured to receive a time of arrival of the selected one or more other users (that may also include the selected one or more other caregivers at the subsequent time instance) from the server 116.

In accordance with an embodiment, the microprocessor 202 may be configured to receive instruction information from the one or more other electronic devices (such as the other electronic device 110) in response to the communicated alert information at the one or more time instances. The received instruction information may be outputted via a wearable device of the one or more sensing devices 104, the mobile device 102b, and/or a speaker communicatively coupled to the IVI device 102a.

In accordance with an embodiment, the selected one or more caregivers, such as the caregiver 114 nearest to the vehicle 106, may provide an input to launch the IVI application by use of the display 224, on arrival at the emergency scene spot. The arrival of the one or more caregivers at the emergency scene spot may occur in response to the communicated alert information. The emergency scene spot may correspond to the current location of the impaired user, such as the driver 108, where the selected one or more caregivers provide an emergency medical assistance, such as a first aid, to the driver 108. The selected one or more caregivers may further provide information related to the health condition of impaired user as observed during a physical check-up of the impaired driver 108, by use of the IVI application.

In accordance with an embodiment, the microprocessor 202 may be configured to transmit the received information, via the IVI application, to other pre-defined medical emergency services, such as a hospital and/or the ambulance service provider, in the vicinity of the impaired driver 108. In accordance with an embodiment, the transmission of the received information may occur automatically based on an availability of a desired facility and/or a medical specialty that may be required for treatment of the impaired driver 108.

In accordance with an embodiment, the microprocessor 202 may be configured to send one or more control commands to the ECU 206 or the powertrain control system 210. The ECU 206 may then be operable to control a speed of the vehicle 106, stop the vehicle 106, control steering of the vehicle 106 by use of the steering system 218, and/or establish communication with the server 116 to communicate the alert information, as described previously. The one or more control commands may be sent via the in-vehicle network 216, such as the CAN bus. The control of the one or more functions, such as temperature and humidity control, of the vehicle 106 may be performed in response to the received one or more control commands from the microprocessor 202 or the ECU 206.

In accordance with embodiment, the microprocessor 202 may be configured to send one or more control commands to the ECU 206 to enable automatic control of steering of the vehicle 106, to drive the vehicle 106 (in an autonomous driving mode) to a medical care center in a vicinity of the vehicle 106. The automatic control of steering of the vehicle 106 may occur when the driver 108 is detected to be in a critical health condition which prohibits the driver 108 to drive the vehicle 106. For example, when an abnormally low blood sugar level is detected for the driver 108, the vehicle 106 may be switched to autonomous mode, and may be automatically driven to a nearest convenient store to avail suitable medicine. During the course of movement of the vehicle 106, a horn may be automatically applied to warn others of the medical emergency or the risky situation. In such a case, the vehicle 106 may automatically park itself and honk to alert nearby pedestrians or the store visitor to find out about the vehicle 106 and/or the driver 108 that needs medical assistance.

In an another example, an elderly driver may experience a Transient Ischemic Attack (TIA) that is considered to be a mild stroke, and may lose consciousness. In such a situation, when the microprocessor 202 detects the TIA based on the received sensor data, the microprocessor 202 may be configured to send one or more control commands to the ECU 206 to enable automatic control of steering of the vehicle 106, to drive the vehicle 106 (in an autonomous driving mode) to a nearest hospital with neurology expertise. On its course towards the nearest hospital, the microprocessor 202 may be configured to communicate the alert information related to the TIA condition, and other data received from the one or more sensing devices 104 to the hospital emergency response (ER) systems. This may enable the ER personnel to have a better perspective, and/or better knowledge about occurrence of events prior to, during, or post occurrence of the medical emergency, past-events, and/or medical history of the elderly driver. This may enable the ER personnel to prepare for the treatment in advance and/or may improve evacuation time as compare to the known "911" ER method.

Figure 3:
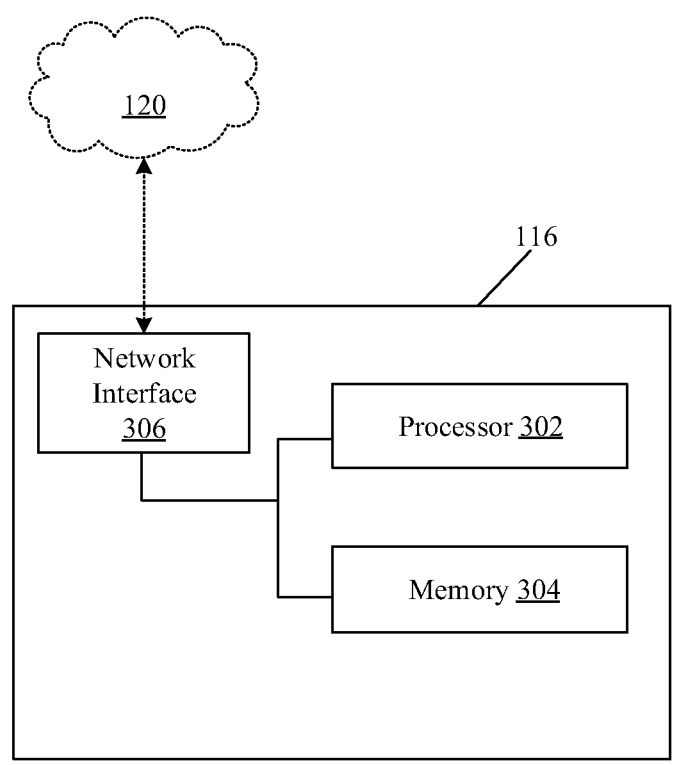
FIG. 3 is a block diagram that illustrates an exemplary server, in accordance with an embodiment of the disclosure.

FIG. 3 is a block diagram that illustrates an exemplary server, in accordance with an embodiment of the disclosure. FIG. 3 is explained in conjunction with elements from FIGS. 1 and 2. With reference to FIG. 3, there is shown the server 116. The server 116 may comprise one or more processors, such as a processor 302, a memory 304, and a network interface 306.

The processor 302 may be connected to the memory 304 and the network interface 306. The network interface 306 may be operable to communicate with one or more electronic devices, such as the electronic device 102 and the other electronic device 110 under the control of the processor 302, via the second communication network 120. The network interface 306 may be further operable to communicate with the one or more other communication mediums associated with emergency service providers, via the second communication network 120.

The processor 302 may comprise suitable logic, circuitry, interfaces, and/or code that may be operable to execute a set of instructions stored in the memory 304. The processor 302 may be implemented, based on a number of processor technologies known in the art. Examples of the processor 302 may be an X86-based processor, a RISC processor, an ASIC processor, a CISC processor, a CPU, a microcontroller, and/or other processors or circuits.

The memory 304 may comprise suitable logic, circuitry, and/or interfaces that may be operable to store a machine code and/or a set of instructions with at least one code section executable by the processor 302. In an embodiment, the memory 304 may be configured to pre-store navigation maps of road networks, and profiles of the caregivers. Examples of implementation of the memory 304 may include, but are not limited to, Random Access Memory (RAM), Read Only Memory (ROM), Hard Disk Drive (HDD), Flash memory, a Secure Digital (SD) card, and/or other solid-state storage.

The network interface 306 may comprise suitable logic, circuitry, interfaces, and/or code that may be operable to communicate with the electronic device 102 and one or more other electronic devices, such as the other electronic device 110, under the control of the processor 302. The network interface 306 may be further operable to communicate with the one or more other communication mediums associated with the emergency services providers, such as a hospital, via the second communication network 120, under the control of the processor 302. The network interface 306 may implement known technologies to support wireless communication of the electronic device 102 and one or more other electronic devices, such as the other electronic device 110, with the second communication network 120. The network interface 306 may include various components, examples of which may include, but are not limited to, an antenna, a RF transceiver, one or more amplifiers, one or more oscillators, a digital signal processor, and/or a coder-decoder (CODEC) chipset. The network interface 306 may communicate, via wireless communication, with networks and by use of one or more communication protocols similar to that described above for the second communication network 120 (FIG. 1).

In operation, the processor 302 may be configured to receive sensor data associated with the driver 108 of the vehicle 106, by use of the network interface 306. The sensor data may be received from the electronic device 102 or via the wireless communication system 214 under the control of the electronic device 102, such as the IVI device 102a. In accordance with an embodiment, instead of the electronic device 102, the processor 302 may be configured to detect a change, such as an abnormal change, in the health condition of the driver 108 based on the received sensor data. In such an embodiment, the processor 302 may be configured to select one or more caregivers, such as the caregiver 114, based on profiles of the one or more caregivers. The profiles of the group of caregivers may be pre-stored at the memory 304 of the server 116.

In accordance with an embodiment, the profiles of the group of caregivers may be received from the one or more other electronic devices such as the other electronic device 110, associated with the group of caregivers. For example, the profile of the caregiver 114 may be transferred to the other IVI device 110a of the other vehicle 112 from the other mobile device 110b, such as a smartphone, of the caregiver 114. In case of a care sharing scenario, a profile of another occupant (another caregiver, such as a doctor) of the other vehicle 112 may also be transferred to the other IVI device 110a from a portable device. The portable device may be associated with the other occupant in such a case. The other IVI device 110a may then communicate the received profile(s) of the caregiver 114 or the other occupant to the server 116 by use of a wireless communication system of the other vehicle 112.

In accordance with an embodiment, the processor 302 may be configured to generate alert information to be communicated to the one or more other electronic devices associated with the selected one or more caregivers. The alert information may correspond to the detected change in the health condition of the driver 108. In accordance with an embodiment, the processor 302 may be configured to communicate an alert to the electronic device 102 based on the generated alert information, by use of the network interface 306. The alert may be communicated for the driver 108 to indicate the detected change in the health condition of the driver 108. Alternatively, in accordance with an embodiment, the sensor data associated with the driver 108 in the vehicle 106 may not be received by the processor 302. In such an embodiment, the alert information that corresponds to the detected change in the health condition of the driver 108, may be received from the electronic device 102 associated with the driver 108.

In accordance with an embodiment, the processor 302 may be configured to determine the one or more other electronic devices, such as the other electronic device 110 associated with the selected one or more caregivers, based on the profiles of the selected one or more caregivers. The processor 302 may be configured to communicate the generated or the received alert information to the determined one or more other electronic devices associated with the selected one or more caregivers.

In accordance with an embodiment, the processor 302 may be configured to customize the received alert information based on the profiles of the one or more caregivers. Subsequently, the processor 302 may be configured to communicate the customized alert information to the one or more other electronic devices associated with the one or more caregivers. The customization may correspond to a change in the target caregiver for the communication, based on updated position of the one or more caregivers, availability of the one or more caregivers, and/or navigation map data used for road travel. The customization may also correspond to a change in the target caregiver for the communication, based on a severity level of the detected health condition of the driver 108. In accordance with an embodiment, the customization may correspond to change in current location of the driver 108 and/or other changes of the received alert information. For instance, one selected caregiver may be a doctor with an expertise in cardiovascular domain, whereas another selected caregiver may have an expertise in another domain, such as in neurosurgery domain. In such an instance, the received alert information may be changed in accordance with the profile, such as type of expertise, of the selected caregiver. Further, in instances when the selected caregiver is not a doctor, the received alert information may be changed to a basic instruction so that the selected caregiver may not experience a difficulty to understand the customized alert information communicated to such selected caregiver(s).

In accordance with an embodiment, the processor 302 may be configured to receive instruction information from the one or more other electronic devices associated with the selected one or more caregivers, in response to the communicated alert information. The instruction information may correspond to medical advisory instructions provided by the selected one or more caregivers. The processor 302 may be further configured to communicate the received instruction information to the electronic device 102 associated with the driver 108.

In accordance with an embodiment, the processor 302 may be configured to receive one or more responses, such as an acknowledgement to provide assistance, from the one or more other electronic devices, such as the other electronic device 110, associated with the selected one or more caregivers. The processor 302 may be configured to determine a time of arrival of the selected one or more caregivers to the driver 108. The time of arrival may be determined based on the received one or more responses and vehicle data of the vehicle 106 and the one or more other vehicles associated with the selected one or more caregivers. The vehicle data may include current position, speed, direction of travel, and lane information of the vehicle 106 and the one or more other vehicles. The time of arrival may be determined based on the navigation map data pre-stored at the memory 304.

In accordance with an embodiment, the processor 302 may be configured to communicate with the selected one or more caregivers to establish coordination among the selected one or more caregivers to provide medical assistance to the driver 108 in case of the medical emergency. The processor 302 may be configured to set an order of arrival of the selected one or more caregivers, based on the established coordination with the selected one or more caregivers.

Figure 4A:
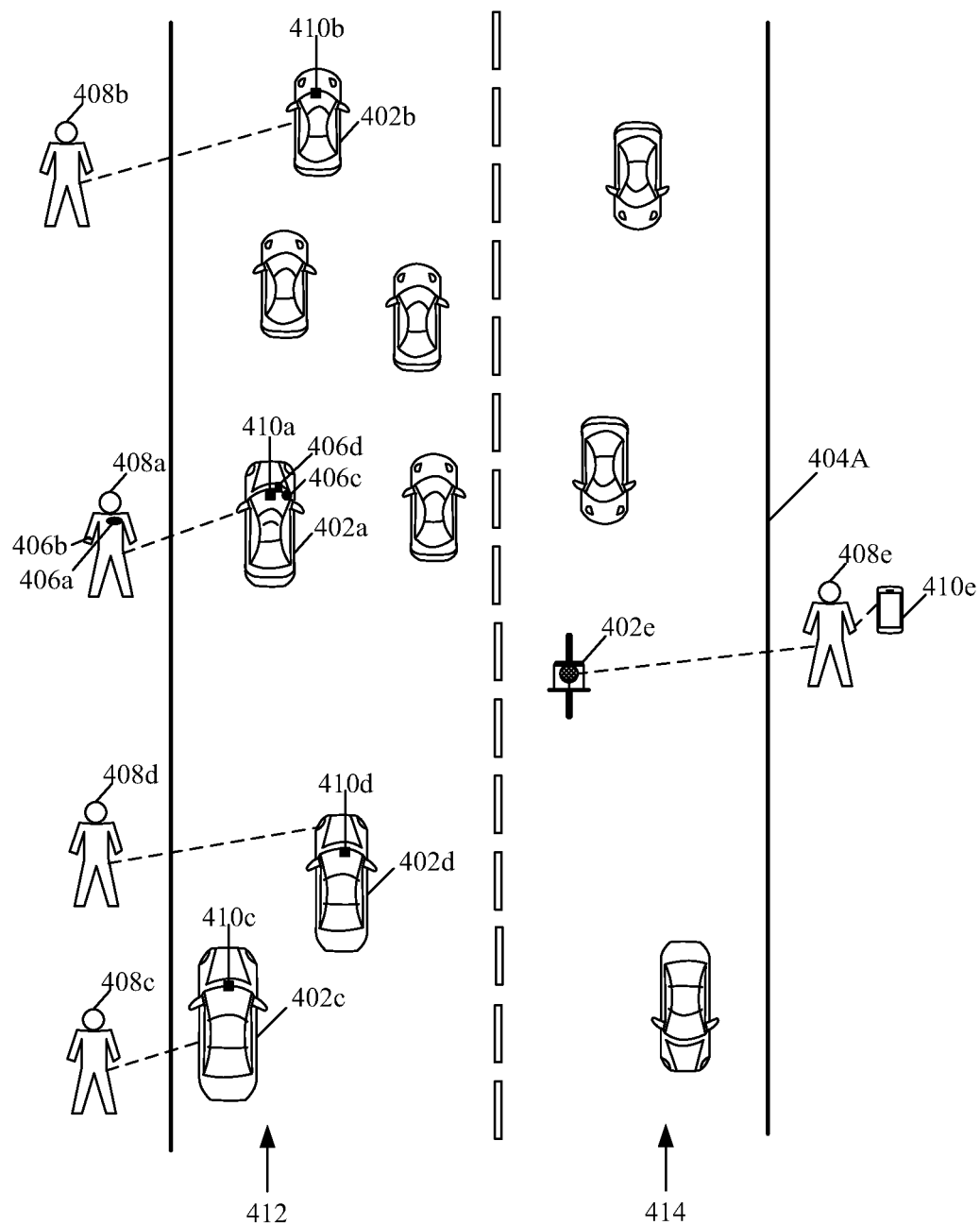
FIG. 4A illustrates a first exemplary scenario for implementation of the disclosed system and method to provide assistance during a medical emergency, in accordance with an embodiment of the disclosure.

FIG. 4A illustrates a first exemplary scenario for implementation of the disclosed system and method to provide assistance during a medical emergency, in accordance with an embodiment of the disclosure. FIG. 4A is explained in conjunction with elements from FIGS. 1, 2, and 3. With reference to FIG. 4A, there is shown a plurality of vehicles 402 that may traverse along a road portion 404A. The plurality of vehicles 402 may include one or more cars, such as a first car 402a, a second car 402b, a third car 402c, and a fourth car 402d, and one or more motorbikes, such as a motorbike 402e.

There is further shown an implantable cardioverter-defibrillator (ICD) 406a implanted into a first user 408a. There is also shown a smart-band 406b worn by the first user 408a, a sweat sensor 406c installed on the steering wheel (not shown) of the first car 402a, and a camera 406d mounted on dashboard (not shown) of the first car 402a. The first user 408a may drive the first car 402a that may include a first electronic device 410a. The other users, such as a second user 408b, a third user 408c, a fourth user 408d, and a fifth user 408e may be registered caregivers.

In accordance with the first exemplary scenario, the second user 408b may be associated with a second electronic device 410b, such as an ECU of the second car 402b. The third user 408c may be associated with a third electronic device 410c, such as an in-vehicle infotainment unit of the third car 402c. The fourth user 408d may be associated with a fourth electronic device 410d, such as an ECU of the fourth car 402d. The fifth user 408e may be associated with a fifth electronic device 410e, such as a smartphone. The first electronic device 410a may correspond to the IVI device 102a (FIGS. 1 and 2). The second electronic device 410b, the third electronic device 410c, the fourth electronic device 410d, and the fifth electronic device 410e may correspond to the one or more other electronic devices, such as the other electronic device 110 (FIG. 1). The implantable cardioverter-defibrillator (ICD) 406a, the smart-band 406b, the sweat sensor 406c, and the camera 406d may correspond to the one or more sensing devices 104 (FIG. 1).

In operation, the first electronic device 410a may be configured to receive sensor data associated with the first user 408a from the one or more sensing devices 104, such as the ICD 406a, the smart-band 406b, the sweat sensor 406c, and/or the camera 406d. The sensor data may comprise health parameters, such as blood pressure, heart rate, cardiac rhythm values, gender information, ECG data, palm sweating information, and/or skin color change information. The first electronic device 410a may be configured to detect an acute myocardial infarction of the driver 108 based on the received sensor data. In accordance with an embodiment, the first electronic device 410a may be configured to analyze the profiles of the group of caregivers stored at the first electronic device 410a. In accordance with the first exemplary scenario, the profiles of the group of caregivers may be provided as given in Table 1, as follows:

TABLE 1

| Profile_ID | User_name | Contact_address | Contact_number | Professional_experience_Yrs | Expertise_level | Type_of_expertise | Current_position | Electronic_device_identifier | Vehicle_identifier | Availability | Service_rating |
|---|---|---|---|---|---|---|---|---|---|---|---|
| 1 | B | BX | ... | 10 | 3 | Cardiologist | X1, Y1 | B11 | B22 | Yes | Null |
| 2 | C | CX. | ... | 3 | 2 | Neurologist | X2, Y2 | C11 | C22 | Yes | 4 |
| 3 | D | DX | ... | 11 | 3 | Cardiologist | X3, Y3 | D11 | D22 | Yes | 5 |
| 4 | E | EX | ... | 10 | 3 | Cardiologist | X4, Y4 | E11 | E22 | Yes | Null |
| 5 | F | FX | ... | 4 | 3 | Cardiologist | X5, Y5 | F11 | F22 | Yes | Null |
| ... | ... | ... | ... | ... | ... | ... | ... | ... | ... | ... | ... |
| N | ... | ... | ... | ... | 1 | Endocrinologist | ... | ... | ... | ... | ... |

In accordance with the Table 1, the profiles of the group of caregivers may comprise parameters, such as user name, contact address, contact number, professional experience in number of years, expertise level (such as start level "1", medium level "2", and expert level "3") of caregiver, type of expertise, current position of the caregiver, identifier of electronic device associated with respective caregiver, and/or identifier of vehicle associated with respective caregiver. In accordance with an embodiment, other parameters, such as user availability <yes> of respective caregiver to provide assistance, and/or a service rating, such as from lowest satisfaction level "1" to highest satisfaction level "5" ratings, may be provided based on historical data or user-satisfaction service level in accordance with past experience with the respective caregivers. For example, the profile (Profile ID: 1) of the second user 408b may comprise parameters, such as user name <B>, contact address <BX>, contact number <22222222>, professional experience <10 years>, expertise level <3>, type of expertise <cardiologist>, current position <latitude "X2"; longitude "Y2">, electronic device identifier <B11> associated with the second electronic device 410b, and/or vehicle identifier <B22> associated with the second car 402b. In accordance with an embodiment, other parameters, such as user availability <yes>, and/or service rating <5>, may also be provided in the profile of the second user 408b.

In accordance with an embodiment, the electronic device 102 may be configured to select one or more caregivers, such as the second user 408b and the fourth user 408d, based on the profiles of the second user 408b and the fourth user 408d. The profiles of the second user 408b and fourth user 408d may be identified to be relevant to handle the medical emergency caused due to the detected abnormal health condition, such as the detected acute myocardial infarction, of the first user 408a. Based on the analysis, it may be identified that the second user 408b and the fourth user 408d traverses in a vicinity of the first user 408a during the medical emergency. Further, the expertise type, such as "cardiologists", and/or the availability status of the second user 408b and the fourth user 408d may indicate a high propensity for the selected one or more caregivers to provide quick and reliable assistance in the medical emergency.

In accordance with an embodiment, based on the analysis of the profiles of the group of caregivers, the profile (Profile ID: 2) of the third user 408c may indicate that the third user 408c in the third car 402c is in the vicinity of the first user 408a at the time of detection of medical emergency. However, the third user 408c may not be selected due to a mismatch in the type of expertise, as the profile of the third user 408c indicates that the third user 408c is a "neurologist".

In accordance with an embodiment, the parameters of lane information and/or direction of travel may also be considered for the selection of the one or more caregivers. For example, the fifth user 408e may not be selected as the profile (Profile ID: 4) of the fifth user 408e may indicate that the fifth user 408e traverses in another lane, such as the second lane 414, and direction of travel may be opposite to the direction of travel of the first user 408a in the first car 402a. Other than the profiles of the second user 408b, the third user 408c, the fourth user 408d, and the fifth user 408e, the profiles of other caregivers of the group of caregivers may indicate that other caregivers are not in the vicinity of the first user 408a, and thus may not be selected. In other words, electronic devices associated with the other caregivers may be beyond a pre-determined proximity range, such as "300 meters", from the first electronic device 410a associated with the first user 408a.

In accordance with an embodiment, the first electronic device 410a may be configured to communicate the alert information to one or more other electronic devices, such as the second electronic device 410b and the fourth electronic device 410d, associated with the selected one or more caregivers. In this case, the communicated alert information may include metadata associated with the detected change in the health condition, such as the acute myocardial infarction, of the first user 408a and a current location of the first user 408a.

In accordance with an embodiment, the metadata may also comprise the health parameters, such as blood pressure, heart rate, sweating information, pain information, and/or time of occurrence of the acute myocardial infarction. The health parameters included in the alert information corresponds to the health parameters associated with the first user 408a received prior to, during, and/or post the detection of the acute myocardial infarction. In accordance with an embodiment, the metadata may also comprise user identification, vehicle identification, and/or friends and family member identification information associated with the first user 408a. The user identification information may include user name, age, gender, height, weight, and/or a photograph of the first user 408a. The vehicle identification information may include vehicle color, vehicle type, lane information on which the vehicle (such as the first car 402a) traverses, a direction of travel of the vehicle, vehicle speed, vehicle license plate number, associated with the vehicle, such as the first car 402a driven by the first user 408a. The friends and family member identification may include name, contact address, and/or contact number of the respective people.

In accordance with an embodiment, the communicated alert information may also include a video of the driver 108 captured by one of the in-vehicle sensors, such as the camera 406d. The video may indicate the health condition of the first user 408a during the medical emergency situation. The communicated alert information may enable the selected one or more caregivers, such as the second user 408b and the fourth user 408d, to be ready to provide first aid to the impaired first user 408a.

In accordance with an embodiment, the first electronic device 410a may be configured to communicate the alert information directly to the second car 402b and the fourth car 402d, via the vehicular communication network 122, such as a V2V communication. In an instance, the first electronic device 410a may be configured to communicate the alert information to the server 116, via the second communication network 120. Instead of the first electronic device 410a, the server 116 may then determine the one or more other electronic devices, such as the second electronic device 410b and the fourth electronic device 410d, associated with selected one or more caregivers, based on the profiles of the caregivers pre-stored at the server 116. In such an instance, the server 116 may be configured to communicate the received alert information to the determined one or more other electronic devices, such as the second electronic device 410b and the fourth electronic device 410d.

Figure 4B:
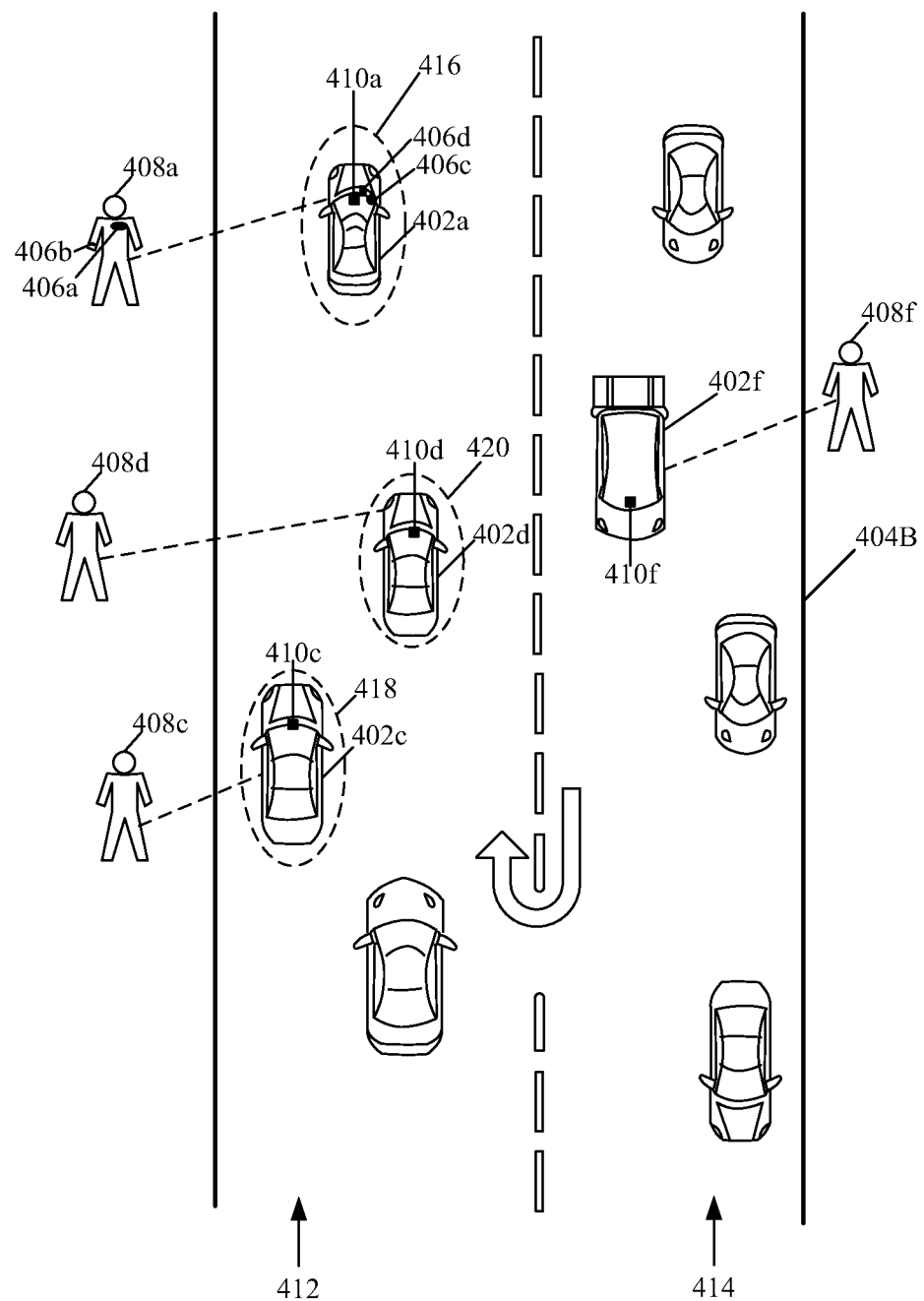
FIG. 4B illustrates a second exemplary scenario for implementation of the disclosed system and method to provide assistance during a medical emergency, in accordance with an embodiment of the disclosure.

FIG. 4B illustrates a second exemplary scenario for implementation of the disclosed system and method to provide assistance during a medical emergency, in accordance with an embodiment of the disclosure. FIG. 4B is explained in conjunction with elements from FIGS. 1, 2, 3, and 4A, and depict sequence of operations from FIG. 4A at another time instance. With reference to FIG. 4B, there is shown updated positions 416, 418 and 420 of the first car 402a, the third car 402c, and the fourth car 402d at another road portion 404B. The plurality of vehicles 402 may further include one or more other vehicles, such as a van 402f associated with a sixth user 408f. The sixth user 408f may be a registered medical assistant with an expertise in handling cardiac emergencies.

In accordance with the second exemplary scenario, the sixth user 408f may drive the van 402f in the second lane 414. The other road portion may include a U-turn ahead of the current position of the sixth user 408f who may be associated with a sixth electronic device 410f, such as an ECU. In accordance with an embodiment, the alert information may be communicated at one or more time instances for a pre-defined duration.

In accordance with embodiment, at a subsequent time instance, the first electronic device 410a may be configured to further select one or more other caregivers, such as the sixth user 408f, based on the profiles of the caregivers, such as the profile (Profile ID: 5 (Table 1)) of the sixth user 408f. In accordance with an embodiment, the profiles of the caregivers may be dynamically updated based on the vehicle data, such as current vehicle position, received from one or more connected vehicles in the vicinity of the updated position 416 of the first car 402a associated with the first user 408a. The profile of the sixth user 408f may indicate that the sixth user 408f is in the vicinity of the first user 408a from the updated position 416 of the first car 402a driven by the first user 408a. The sixth user 408f may be selected due to a match in the type of expertise, as the profile of the sixth user 408f indicates that the sixth user 408f is a "cardiologist". Further, although the parameters of lane information indicate a different lane (the second lane 414) from the current lane of the first car 402a, and an opposite direction of travel, the navigation map data may indicate the U-turn ahead of the current position of the van 402f. In instances when the navigation map data indicates a turn ahead or a suitable passage along a road portion that increases the propensity for a potential caregiver, such as the sixth user 408f in this case, to reach the emergency scene to assist an impaired user, such as the first user 408a, then the potential caregiver (the sixth user 408f in this case) may be selected. In such an instance, the first electronic device 410a may be further configured to communicate the alert information to the sixth electronic device 410f, via the second communication network 120 or the vehicular communication network 122.

In accordance with an embodiment, the first electronic device 410a may be further configured to communicate the alert notification with current location information of the first user 408a to a nearest hospital, an ambulance service provider, and/or pre-configured one or more other mobile devices associated with friends, family members, and/or relatives of the first user 408a.

Figure 5A:
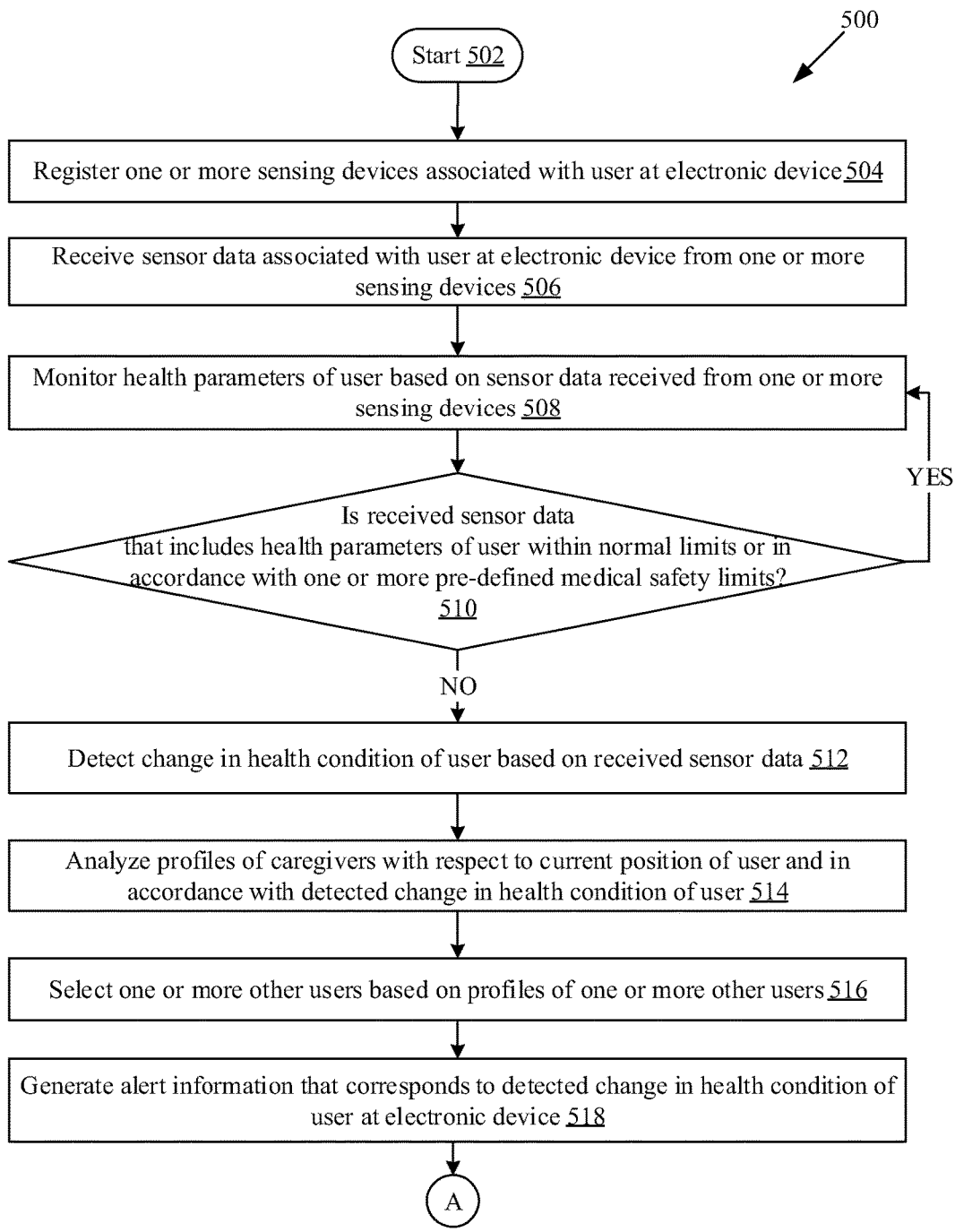
FIGS. 5A and 5B collectively depict a first flow chart that illustrates an exemplary method to provide assistance during a medical emergency, in accordance with an embodiment of the disclosure.
Figure 5B:
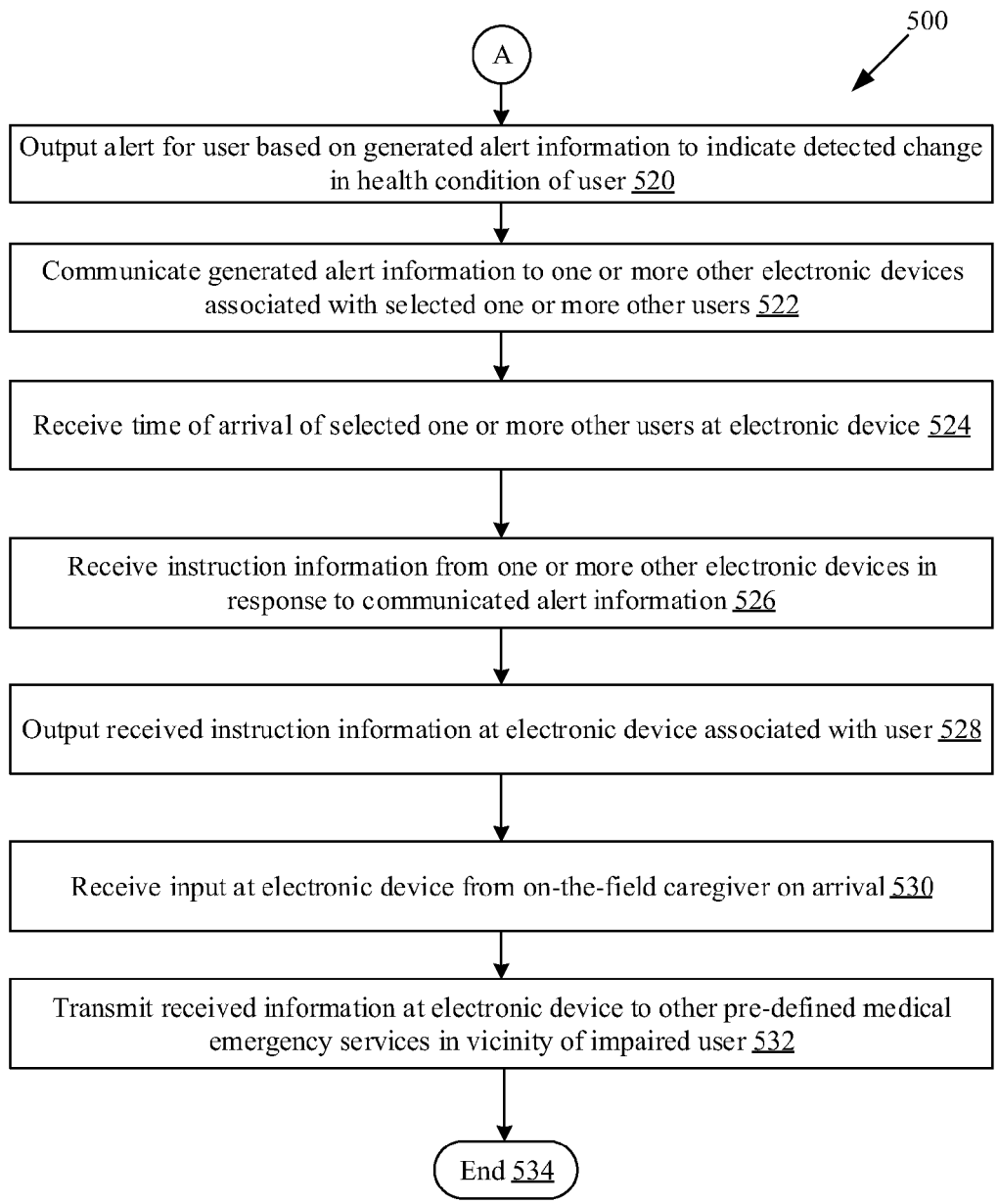

FIGS. 5A and 5B collectively depict a first flow chart 500 that illustrates an exemplary method to provide assistance during a medical emergency, in accordance with an embodiment of the disclosure. With reference to FIGS. 5A and 5B, there is shown the first flow chart 500. The first flow chart 500 is described in conjunction with FIGS. 1, 2, 3, 4A and 4B. The method starts at step 502 and proceeds to step 504.

At step 504, the one or more sensing devices 104 associated with a user, such as the driver 108 or the first user 408a, may be registered at an electronic device, such as the electronic device 102 (FIG. 1) or the first electronic device 410a. For example, the one or more sensing devices 104, such as the ICD 406a, the smart-band 406b, and/or the sweat sensor 406c, may be communicatively coupled to the first electronic device 410a.

At step 506, sensor data associated with the user may be received at the electronic device 102 (or the first electronic device 410a) from the one or more sensing devices 104. In accordance with an embodiment, the sensor data may comprise health parameters, such as blood pressure, heart rate, cardiac rhythm values, gender information, blood glucose data, ECG data, sweating information, and/or skin color change information. The received sensor data may indicate a health condition of the user, such as the driver 108 or the first user 408a.

At step 508, health parameters of the user may be monitored based on the sensor data received from the one or more sensing devices 104. The monitoring may be based on a periodic receipt of the sensor data from the one or more sensing devices 104. At step 510, it may be checked whether the received sensor data that includes the health parameters of the user (such as the driver 108) is within normal limits or in accordance with one or more pre-defined medical safety limits. In instances when the received sensor data is not within normal limits or not in accordance with one or more pre-defined medical safety limits, the control passes to step 512. In instances when the received sensor data is within normal limits and/or in accordance with one or more pre-defined safety limits, the control may pass back to the step 508.

At step 512, a change, such as an abnormal change, in health condition of the user (such as the driver 108 or the first user 408a) may be detected based on the received sensor data. In accordance with an embodiment, the detection of the change in the health condition of the user may be further based on a health profile of the user. The health profile may include medical history data of the user (such as the driver 108 or the first user 408a). In accordance with an embodiment, the medical history data may correspond to self-declaration of medical information provided by the user.

At step 514, profiles of caregivers may be analyzed with respect to current position of the user and in accordance with the detected change in the health condition of the user. The analysis may be performed to identify relevant caregivers in the vicinity of the user (such as the driver 108 or the first user 408a). An example of the profiles of caregivers has been described in the Table 1 of FIG. 4A.

At step 516, one or more other users (such as the caregiver 114 (FIG. 1) or the second user 408b and the fourth user 408d (FIG. 4A)) may be selected based on profiles (such as Profile IDs: 1 and 3 (Table 1)) of the one or more other users. In accordance with an embodiment, the profiles of the one or more other users may correspond to the profiles of caregivers that may be stored at the electronic device (such as the electronic device 102 or the first electronic device 410a). The profiles of the caregivers may include at least the expertise level, the type of expertise, the availability, an/or current position information of the caregivers that may be utilized for the selection of the one or more other users, as described and shown in FIGS. 4A and 4B as an example.

At step 518, alert information that corresponds to the detected change in the health condition of the user (such as the driver 108 or the first user 408a) may be generated at the electronic device (such as the electronic device 102 or the first electronic device 410a). At step 520, an alert for the user may be outputted based on the generated alert information to indicate the detected change, such as a high blood sugar level, a potential heart attack, a hyperhidrosis condition, and/or other abnormal change, in the health condition of the user. The output may be audio, text, haptic, and/or video output provided via a wearable device (such as the smart-band 406b (FIG. 4A)), a mobile device (such as the mobile device 102b (FIG. 1)), and/or an in-vehicle electronic device (such as via the display 224 or the speakers associated with the IVI device 102a).

At step 522, the generated alert information may be communicated to one or more other electronic devices (such as the other electronic device 110 or the second electronic device 410b and the fourth electronic device 410d), associated with the selected one or more other users (such as the caregiver 114 or the second user 408b and the fourth user 408d). The generated alert information may be communicated to the one or more other electronic devices, via the second communication network 120 and/or the vehicular communication network 122 (such as V2V communication).

In accordance with an embodiment, the communicated alert information may comprise metadata associated with the detected change in the health condition of the user and current location of the user. In accordance with an embodiment, the metadata may comprise one or more health parameters of the user received prior to, during, and/or post the detected change in the health condition of the user (such as the driver 108 or the first user 408a), as described in FIGS. 1 and 2. The communicated alert information may enable the selected one or more other users (such as the caregiver 114 or the second user 408b) to be ready to provide a first aid to the impaired user. In accordance with an embodiment, the alert information may be communicated at one or more time instances for a pre-defined time interval. For example, as shown and described in FIG. 4B, another caregiver, such as the sixth user 408f may be selected based on updated position of the first user 408a that may be in motion. The selection of one or more other caregivers at a subsequent time instance may be further based on updated distance information of the one or more caregivers from the user (such as the first user 408a). In such instances, the alert information may be further communicated to the one or more other caregivers selected at the subsequent time instance of the pre-determined time interval.

At step 524, a time of arrival of the selected one or more other users (that may also include the selected one or more other caregivers at the subsequent time instance) may be received at the electronic device (such as electronic device 102 or the first electronic device 410a). In accordance with an embodiment, the time of arrival may be received from the server 116, as described in FIG. 3.

At step 526, instruction information from the one or more other electronic devices may be received in response to the communicated alert information at the one or more time instances. For example, instruction information, such as "Hold your <the driver 108> chest in a 60 degrees angle", may be received. Examples of the one or more other electronic devices may include the other electronic device 110 associated with the caregiver 114 (FIG. 1), the second electronic device 410b associated with the selected second user 408b, the fourth electronic device 410d associated with the selected fourth user 408d, or the sixth electronic device 410f associated with the selected sixth user 408f (FIGS. 4A and 4B). In accordance with an embodiment, the instruction information may be audio, text and/or video instructions.

At step 528, the received instruction information may be outputted at the electronic device (such as the electronic device 102 or the first electronic device 410a) associated with the user. The output may be generated via a wearable device of the one or more sensing devices 104, the mobile device 102b, and/or a speaker communicatively coupled to the IVI device 102a. For example, the mobile device 102b may output the instruction information as an audio message to instruct the driver 108 to stop the vehicle 106 at a safe location along a road portion.

At step 530, on arrival of the one or more other users, input may be received at the electronic device (such as the IVI device 102a or the first electronic device 410a) from at least an on-the-field caregiver (such as a registered physician) of the one or more other users. The on-the-field caregiver may be one of the selected one or more other users (such as the caregiver 114 or the second user 408b), who may arrive at the current location of the impaired user (such as the driver 108 or the first user 408a) to provide an emergency medical assistance, such as first aid, to the impaired user. The input may correspond to information related to the health condition of impaired user as observed during a physical check-up of the impaired user by the on-the-field caregiver who arrived in response to the communicated alert information. For example, on arrival of the on-the-field caregiver, and after the provision of the first aid by the caregiver, the information related to the health condition of the impaired user (such as the impaired driver 108) may be provided via the display 224 (such as touch screen based input) associated with the IVI device 102a used in the vehicle 106. The application pre-stored at the IVI device 102a may be launched, via the display 224, to input the information related to the health condition of the impaired user.

At step 532, the received information at the electronic device may be transmitted to other pre-defined medical emergency services, such as a hospital, and/or the ambulance service provider, in the vicinity of the impaired user. In accordance with an embodiment, transmission of the received information may occur automatically based on an availability of a desired facility and/or a medical specialty that may be required for treatment of the impaired user as per the detected and/or observed heath condition of the impaired user. The control may pass to the end step 534.

Figure 6:
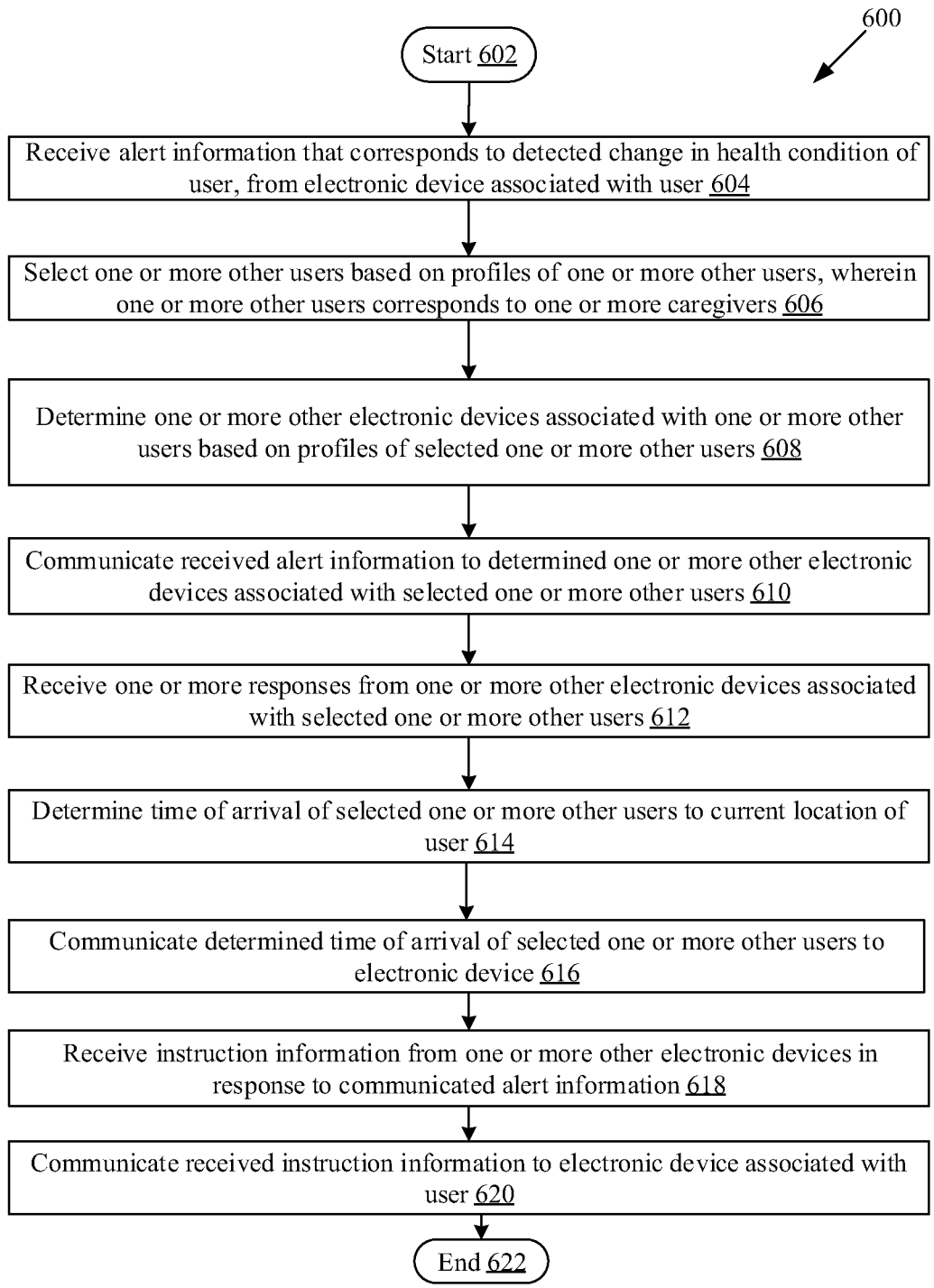
FIG. 6 depicts a second flow chart that illustrates another exemplary method to provide assistance during a medical emergency, in accordance with an embodiment of the disclosure.

FIG. 6 depicts a second flow chart that illustrates an exemplary method to provide assistance during a medical emergency, in accordance with an embodiment of the disclosure. With reference to FIG. 6, there is shown the second flow chart 600 that may be implemented in a server, such as the server 116. The second flow chart 600 is described in conjunction with FIGS. 1, 2, 3, 4A and 4B. The method starts at step 602 and proceeds to step 604.

At step 604, alert information that corresponds to a detected change in a health condition of a user, such as the driver 108 or the first user 408a, may be received from an electronic device (such as the electronic device 102 (FIG. 1) or the first electronic device 410a (FIG. 4A)) associated with the user. The received alert information may comprise the metadata associated with the detected change in the health condition of the user and current location of the user. In accordance with an embodiment, the metadata may also comprise one or more health parameters of the user received prior to, during, and/or post the detected change in the health condition of the user (such as the driver 108 or the first user 408a), as described in FIGS. 1, 3, 4A, and 4B.

At step 606, one or more other users (such as the caregiver 114 (FIG. 1) or the second user 408b and the fourth user 408d (FIG. 4A)) may be selected based on the profiles (such as Profile IDs: 1 and 3 of Table 1) of the one or more other users. The one or more other users may correspond to the one or more caregivers. In accordance with an embodiment, the profiles of the one or more other users may correspond to the profiles of the group of caregivers that may be stored at the server 116. The profiles of the group of the caregivers may include at least the expertise level, the type of expertise, the availability, an/or current position information of the caregivers that may be utilized for the selection of the one or more other users, as described and shown in FIGS. 4A and 4B as an example.

At step 608, one or more other electronic devices (such as the other electronic device 110 or the second electronic device 410b and the fourth electronic device 410d) associated with the selected one or more other users (such as the selected caregiver 114 or the selected second user 408b and/or the fourth user 408d) may be determined based on the profiles of the selected one or more other users.

At step 610, the received alert information may be communicated to the determined one or more other electronic devices (such as the other electronic device 110 or the second electronic device 410b and the fourth electronic device 410d) associated with the selected one or more other users. The received alert information may be communicated to the one or more other electronic devices, via the second communication network 120. In accordance with an embodiment, the received alert information may be customized based on the profiles of the one or more caregivers. Subsequently, the customized alert information may be communicated to the one or more other electronic devices associated with the one or more caregivers. The customization may correspond to a change in the target caregiver for the communication, based on updated position of the one or more caregivers, availability of the one or more caregivers, and/or navigation map data used for road travel, as described in FIG. 3.

At step 612, one or more responses, such as an acknowledgment message with a confirmation of availability, may be received at the server 116 from the one or more other electronic devices associated with selected one or more other users, to provide assistance. At step 614, a time of arrival of the selected one or more other users to a current location of the user may be determined. The time of arrival may be determined based on the received one or more responses, and/or vehicle data, such as current position, speed, direction of travel, and lane information, of the vehicle 106 and the one or more other vehicles associated with the selected one or more caregivers.

At step 616, the determined time of arrival of selected one or more other users (such as the caregiver 114, the second user 408*b*, the fourth user 408*d*, and/or the sixth user 408*f*) may be communicated to the electronic device (such as the electronic device 102 or the first electronic device 410*a*). At step 618, instruction information may be received from the one or more other electronic devices (such as the other electronic device 110 or the second electronic device 410*b* and the fourth electronic device 410) in response to the communicated alert information. In certain instances, a first aid may be provided by not only one or more nearby physicians or medical assistants, but also by nearby public drivers, passengers, or pedestrians (potential caregivers) that may pre-register (such as at the server 116) for the provision of such first aid service. In such instances, instruction information may be received from the potential nearest caregiver(s).

At step 620, the received instruction information may be communicated to the electronic device (such as the electronic device 102 or the first electronic device 410*a*) associated with user (such as the driver 108 or the first user 408*a*). The instruction information may correspond to medical advisory instructions (or other instructions that may be beneficial in such medical emergency situation) provided by the selected one or more caregivers. The control may pass to the end step 622.

In accordance with an embodiment of the disclosure, a method and system (such as the electronic device 102 (FIG. 1)) to provide assistance during a medical emergency is disclosed. The electronic device 102 may comprise one or more circuits (hereafter referred to as the microprocessor 202 (FIG. 2)). The microprocessor 202 may be configured to receive sensor data associated with a user (such as the driver 108 (FIG. 1)) from the one or more sensing devices 104. The microprocessor 202 may be configured to detect a change in health condition of the user based on the received sensor data. The microprocessor 202 may be configured to communicate alert information that corresponds to the detected change to one or more other electronic devices (such as the other electronic device 110 (FIG. 1)), associated with one or more other users (such as the caregiver 114 (FIG. 1)). The one or more other users may be selected based on profiles of the one or more other users.

In accordance with an embodiment, the alert information that corresponds to the detected change in the health condition of the user (such as the driver 108), may be communicated to the server 116. In accordance with an embodiment, the alert information may be communicated to one or more vehicles, such as the other vehicle 112, associated with the one or more other users via vehicle-to-vehicle communication.

In accordance with an embodiment, the communicated alert information may comprise metadata associated with the detected change in the health condition of the user (such as the driver 108) and a current location of the user. The metadata may comprise one or more health parameters of the user received prior to, during, and/or post the detected change in the health condition of the user. In accordance with an embodiment, the alert information may be customized based on the profiles of the one or more other users, such as the caregiver 114.

In accordance with an embodiment, instruction information may be communicated to the user, in response to the detected change in the health condition of the user, based on generating audio, text, and/or video instructions. In accordance with an embodiment, the instruction information may be received from the server 116, and/or the one or more other electronic devices (such as the other electronic device 110) in response to the communicated alert information.

In accordance with an embodiment, the profiles of the one or more other users may comprise an expertise level, a type of expertise, a current position, and/or availability of the one or more other users. In accordance with an embodiment, the electronic device 102 and/or the one or more other electronic devices, such as the other electronic device 110, may be a wearable device, an electronic control unit (ECU) (such as the ECU 206) used in a vehicle, an in-vehicle infotainment device (such as the IVI device 102*a* or the other IVI device 110*a*), a server (such as the server 116), and/or a mobile device (such as the mobile device 102*b* or the other mobile device 110*b*).

In accordance with an embodiment, the ECU 206 may be further configured to control a speed of the vehicle 106, stop the vehicle 106, control steering of the vehicle 106, and/or establish communication with the server 116 to communicate the alert information based on the detected change in the health condition of the user (such as the driver 108). In accordance with an embodiment, the one or more sensing devices 104 may correspond to one or more wearable devices worn by the user (such as the driver 108), one or more in-vehicle sensors, and/or an electronic sensor implanted in the user.

In accordance with an embodiment of the disclosure, a server (such as the server 116 (FIGS. 1 and 3)) is disclosed. The server may comprise one or more circuits (hereafter referred to as the processor 302 (FIG. 3)). The processor 302 may be configured to receive alert information that corresponds to a detected change in a health condition of a user (such as the driver 108 (FIG. 1)), from the electronic device 102 associated with the user. The processor 302 may be configured to determine one or more other electronic devices (such as the other electronic device 110 (FIG. 1)) associated with one or more other users (such as the caregiver 114 (FIG. 1)) to communicate the received alert information based on profiles of the one or more other users. The processor 302 may be configured to communicate the received alert information to the determined one or more other electronic devices associated with the one or more other users.

In accordance with an embodiment, instruction information may be received at the server 116 from the one or more other electronic devices (such as the other electronic device 110) in response to the communicated alert information. The received instruction information may be communicated to the electronic device 102 associated with the user. The server 116 may comprise the memory 304 configured to store the profiles of the one or more other users (such as the group of caregivers).

In accordance with an embodiment, the received alert information may be customized based on the profiles of the one or more other users. The customized alert information may be communicated to the one or more other electronic devices (such as the other electronic device 110) associated with the one or more other users.

In accordance with an embodiment, the received alert information may comprise metadata associated with the detected change in the health condition of the user and a current location of the user. The metadata may comprise one or more health parameters of the user prior to, during, and/or post the detected change in the health condition of the user.

In accordance with an embodiment of the disclosure, a vehicle (such as the other vehicle 112 (FIG. 1)) is disclosed.

The vehicle may comprise an in-vehicle infotainment (IVI) device (such as the other IVI device 110a (FIG. 1)) that may comprise one or more circuits. The one or more circuits, such as a microprocessor, may be configured to receive alert information that corresponds to a detected change in health condition of a user (such as the driver 108 (FIG. 1)) associated with another vehicle (such as the vehicle 106 (FIG. 1)). The one or more circuits may be configured to communicate instruction information to the user, such as the driver 108, based on the received alert information.

In accordance with an embodiment, the alert information may be received from the server 116 and/or the other vehicle (such as the vehicle 106). The received alert information may be customized to generate the instruction information based on a profile of another user (such as the caregiver 114) associated with the vehicle (such as the other vehicle 112) and/or the IVI device (such as the other IVI device 110a).

In accordance with an embodiment, the instruction information may be generated at the IVI device (such as the other IVI device 110a) when the alert information is received by the IVI device. In accordance with an embodiment, the instruction information may be generated at the other mobile device 110b when the alert information is received by the other mobile device 110b. The other mobile device 110b may be configured to customize the received alert information to generate the instruction information. The generated instruction information may be subsequently transmitted to the IVI device (such as the other IVI device 110a).

In accordance with an embodiment, the instruction information may be communicated to the user (such as the driver 108) associated with the other vehicle (such as the vehicle 106) via vehicle-to-vehicle communication. Such communication of the instruction information may occur in response to the detected change in the health condition of the user (such as the driver 108). The communicated instruction information may be outputted at the other vehicle (such as the vehicle 106) as audio, text, and/or video instructions.

In accordance with an embodiment of the disclosure, a vehicle (such as the vehicle 106 (FIGS. 1 and 2)) is disclosed. The vehicle 106 may comprise an in-vehicle infotainment device (such as the IVI device 102a (FIGS. 1 and 2)). The in-vehicle infotainment device comprises one or more circuits (hereafter referred to as the microprocessor 202 (FIG. 2)) that may be communicatively coupled to the one or more sensing devices 104. The microprocessor 202 may be configured to receive sensor data associated with a user (such as the driver 108 (FIG. 1) from the one or more sensing devices 104. The microprocessor 202 may be configured to detect a change in health condition of the user based on the received sensor data. The microprocessor 202 may be configured to communicate alert information that corresponds to the detected change to one or more other electronic devices, such as the other electronic device 110 (FIG. 1), associated with one or more other users, such as the caregiver 114 (FIG. 1). The one or more other users may be selected based on profiles of the one or more other users.

Various embodiments of the disclosure may provide a non-transitory computer readable medium and/or storage medium, with a set of computer-executable instructions stored thereon to cause a machine and/or a computer to control provision of assistance in a medical emergency. The set of computer-executable instructions in an electronic device, such as the electronic device 102 (FIGS. 1 and 2), may cause the machine and/or computer to perform the steps that comprise receipt of sensor data associated with a user (such as the driver 108 (FIG. 1) from the one or more sensing devices 104. A change in health condition of the user may be detected based on the received sensor data. Alert information that corresponds to the detected change may be communicated to one or more other electronic devices, such as the other electronic device 110 (FIG. 1), associated with one or more other users, such as the caregiver 114 (FIG. 1). The one or more other users may be selected based on profiles of the one or more other users.

The present disclosure may be realized in hardware, or a combination of hardware and software. The present disclosure may be realized in a centralized fashion, in at least one computer system, or in a distributed fashion, where different elements may be spread across several interconnected computer systems. A computer system or other apparatus adapted to carry out the methods described herein may be suited. A combination of hardware and software may be a general-purpose computer system with a computer program that, when loaded and executed, may control the computer system such that it carries out the methods described herein. The present disclosure may be realized in hardware that comprises a portion of an integrated circuit that also performs other functions.

The present disclosure may also be embedded in a computer program product, which comprises all the features enabling the implementation of the methods described herein, and which when loaded in a computer system is able to carry out these methods. Computer program, in the present context, means any expression, in any language, code or notation, of a set of instructions intended to cause a system having an information processing capability to perform a particular function either directly, or after either or both of the following: a) conversion to another language, code or notation; b) reproduction in a different material form.

While the present disclosure has been described with reference to certain embodiments, it will be understood by those skilled in the art that various changes may be made and equivalents may be substituted without departure from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

It should be noted that the present disclosure may also take the following configurations.

(1). A system including:
one or more circuits in an electronic device configured to:
receive sensor data associated with a user from one or more sensing devices;
detect a change in health condition of the user based on the received sensor data; and
communicate alert information corresponding to the detected change to one or more other electronic devices associated with one or more other users, in which the one or more other users are selected based on profiles of the one or more other users.

(2). The system according to (1), in which the one or more circuits are configured to communicate the alert information corresponding to the detected change in the health condition of the user to a server.

(3). The system according to (1) or (2), in which the one or more circuits are configured to communicate the alert information corresponding to the detected change in the health condition of the user to one or more vehicles associated with the one or more other users via vehicle-to-vehicle communication.

(4). The system according to any of (1) to (3), in which the one or more circuits are further configured to customize the alert information based on the profiles of the one or more other users.

(5). The system according to any of (1) to (4), in which the communicated alert information includes metadata associated with the detected change in the health condition of the user and/or a current location of the user.

(6). The system according to (5), in which the metadata includes one or more health parameters of the user prior to, during, and/or post the detected change in the health condition of the user.

(7). The system according to any of (1) to (6), in which the one or more circuits are configured to communicate instruction information to the user, in response to the detected change in the health condition of the user, based on generating audio, text and/or video instructions.

(8). The system according to (7), in which the one or more circuits are configured to receive the instruction information from a server, and/or the one or more other electronic devices in response to the communicated alert information.

(9). The system according to any of (1) to (8), in which the profiles of the one or more other users include one or more of: an expertise level, a type of expertise, a current position, and/or availability of the one or more other users.

(10). The system according to any of (1) to (9), in which the electronic device and/or the one or more other electronic devices is one of: a wearable device, an electronic control unit (ECU) used in a vehicle, an in-vehicle infotainment device, a server, and/or a mobile device.

(11). The system according to (10), in which the ECU is further configured to perform one or more of: control a speed of the vehicle, stop the vehicle, control steering of the vehicle, and/or establish communication with a server to communicate the alert information based on the detected change in the health condition of the user.

(12). The system according to any of (1) to (11), in which the one or more sensing devices correspond to one or more of: one or more wearable devices worn by the user, one or more in-vehicle sensors, and/or an electronic sensor implanted in the user.

(13). A server including:
one or more circuits configured to:
receive alert information corresponding to a detected change in a health condition of a user, from an electronic device associated with the user;
determine one or more other electronic devices associated with one or more other users to communicate the received alert information based on profiles of the one or more other users; and
communicate the received alert information to the determined one or more other electronic devices associated with the one or more other users.

(14). The server according to (13), in which the one or more circuits are configured to receive instruction information from the one or more other electronic devices in response to the communicated alert information.

(15). The server according to (14), in which the one or more circuits are configured to communicate the received instruction information to the electronic device associated with the user.

(16). The server according to any of (13) to (15), further including a memory configured to store the profiles of the one or more other users.

(17). The server according to any of (1) to (16), in which the profiles of the one or more other users include one or more of: an expertise level, a type of expertise, a current position, and/or availability of the one or more other users.

(18). The server according to (17), in which the one or more circuits are configured to customize the received alert information based on the profiles of the one or more other users.

(19). The server according to (18), in which the one or more circuits are configured to communicate the customized received alert information to the one or more other electronic devices associated with the one or more other users.

(20). The server according to any of (13) to (19), in which the received alert information includes metadata associated with the detected change in the health condition of the user and a current location of the user.

(21). The server according to any of (1) to (20), in which the metadata includes one or more health parameters of the user received prior to, during, and/or post the detected change in the health condition of the user.

(22). A vehicle including:
an in-vehicle infotainment (IVI) device that includes one or more circuits configured to:
receive alert information corresponding to a detected change in health condition of a user associated with another vehicle; and
communicate instruction information to the user based on the received alert information.

(23). The vehicle according to (22), in which the one or more circuits are configured to receive the alert information from a server and/or the other vehicle.

(24). The vehicle according to (22) or (23), in which the one or more circuits are configured to customize the received alert information to generate the instruction information based on a profile of another user associated with the vehicle and/or the IVI device.

(25). The vehicle according to any of (22) to (24), in which the alert information is received by a mobile device, in which the mobile device is configured to customize the received alert information to generate the instruction information, in which the generated instruction information is transmitted to the IVI device.

(26). The vehicle according to any of (22) to (25), in which the one or more circuits are configured to communicate the instruction information to the user associated with the other vehicle, in response to the detected change in the health condition of the user, via vehicle-to-vehicle communication, in which the communicated instruction information is outputted at the other vehicle as audio, text, and/or video instructions.

It should be understood by those skilled in the art that various modifications, combinations, sub-combinations and alterations may occur depending on design requirements and other factors insofar as they are within the scope of the appended claims or the equivalents thereof.

What is claimed is:

1. A first vehicle, comprising:
   an in-vehicle infotainment (IVI) device that comprises one or more circuits configured to:
      receive alert information corresponding to a detected change in health condition of a second user associated with a second vehicle;
      generate instruction information based on said received alert information, a profile of a first user associated with at least one of said first vehicle or said IVI device, and a health profile of said second user, wherein said health profile includes information related to a medical history of said second user; and
      communicate said instruction information to said second user.

2. The first vehicle according to claim 1, wherein said one or more circuits are further configured to receive said alert information from at least one of a server or said second vehicle.

3. The first vehicle according to claim 1, wherein said alert information is received by a mobile device, wherein said mobile device is configured to customize said received alert information to generate said instruction information, wherein said generated instruction information is transmitted to said IVI device.

4. The first vehicle according to claim 1, wherein said one or more circuits are further configured to communicate said instruction information to said second user associated with said second vehicle, based on said detected change in said health condition of said second user, via vehicle-to-vehicle communication, wherein said communicated instruction information is output at said second vehicle as at least one of audio, text, or video instructions.

* * * * *